(12) United States Patent
Michaeli et al.

(10) Patent No.: US 11,872,074 B2
(45) Date of Patent: *Jan. 16, 2024

(54) NON-INVASIVE DYNAMIC MEASUREMENT OF INTRACRANIAL RESERVE SPACE

(71) Applicants: David Michaeli, Ashkelon (IL); Menashe Michaeli, Vilnius (LT)

(72) Inventors: David Michaeli, Ashkelon (IL); Menashe Michaeli, Vilnius (LT)

(*) Notice: Subject to any disclaimer, the term of this patent is extended or adjusted under 35 U.S.C. 154(b) by 0 days.

This patent is subject to a terminal disclaimer.

(21) Appl. No.: 17/521,989

(22) Filed: Nov. 9, 2021

(65) Prior Publication Data

US 2022/0061800 A1    Mar. 3, 2022

Related U.S. Application Data

(63) Continuation of application No. 16/093,656, filed as application No. PCT/IL2017/050443 on Apr. 10, (Continued)

(51) Int. Cl.
*A61B 8/08* (2006.01)
*A61B 8/06* (2006.01)
(Continued)

(52) U.S. Cl.
CPC .............. *A61B 8/0816* (2013.01); *A61B 8/06* (2013.01); *A61B 8/0808* (2013.01); (Continued)

(58) Field of Classification Search
CPC ....... A61B 8/0816; A61B 8/06; A61B 8/0808; A61B 8/0891; A61B 8/429; A61B 8/4477; A61B 8/488; A61B 8/5207; A61B 8/5223; A61B 8/523; A61B 8/15; A61B 8/42; A61B 8/5269; A61B 5/021; A61B 5/031;
(Continued)

(56) References Cited

U.S. PATENT DOCUMENTS

| | | | | |
|---|---|---|---|---|
| 4,204,547 A | * | 5/1980 | Allocca ................ | A61B 5/0265 600/561 |
| 5,617,873 A | * | 4/1997 | Yost ..................... | A61B 8/0808 33/511 |

(Continued)

*Primary Examiner* — Peter Luong
(74) *Attorney, Agent, or Firm* — Shlomo Horowitz, Esq.; Steven Horowitz

(57) ABSTRACT

System for non-invasive measuring of an intracranial reserve space (ICRS) parameter of a mammalian subject, comprising a multi-frequency ultrasound probe configured, beginning at a start time, to emit and receive ultrasound waves into and the subject's head and to produce a signal of brain tissue pulsation; an instrument configured to non-invasively partially occlude an internal jugular vein (IJV) starting at the start time and including a second ultrasound probe producing a second signal; and a computer system configured to receive the signal, the second signal and the start time, the computer system also configured, using one or more processors, to derive from the signal an intracranial brain tissue pulsation waveform and from the second signal images of the IJV, and to determine a length of time from the start time to a subsequent time at which the waveform is sufficiently compressed so as to exhibit a predefined decline in variability.

20 Claims, 15 Drawing Sheets

Related U.S. Application Data 2017, now Pat. No. 11,166,696, which is a continuation-in-part of application No. 15/098,420, filed on Apr. 14, 2016, now abandoned.

(51) Int. Cl.

| | | |
|---|---|---|
| *A61B 8/00* | (2006.01) | |
| *A61B 8/15* | (2006.01) | |
| *A61B 5/00* | (2006.01) | |
| *A61B 5/021* | (2006.01) | |
| *A61B 5/03* | (2006.01) | |

(52) U.S. Cl.
CPC ............ *A61B 8/0891* (2013.01); *A61B 8/429* (2013.01); *A61B 8/4477* (2013.01); *A61B 8/488* (2013.01); *A61B 8/523* (2013.01); *A61B 8/5207* (2013.01); *A61B 8/5223* (2013.01); *A61B 5/021* (2013.01); *A61B 5/031* (2013.01); *A61B 5/4064* (2013.01); *A61B 5/6814* (2013.01); *A61B 8/15* (2013.01); *A61B 8/42* (2013.01); *A61B 2560/0462* (2013.01); *A61B 2576/026* (2013.01)

(58) Field of Classification Search
CPC ................ A61B 5/4064; A61B 5/6814; A61B 2560/0462; A61B 2576/026
See application file for complete search history.

(56) References Cited

U.S. PATENT DOCUMENTS

| | | |
|---|---|---|
| 6,066,097 A | 5/2000 | Glenn et al. |
| 6,213,380 B1 | 4/2001 | Collins et al. |
| 6,695,784 B1 | 2/2004 | Michaeli |
| 8,109,880 B1 | 2/2012 | Pranevicius et al. |
| 2003/0055337 A1 | 3/2003 | Lin |
| 2003/0060711 A1 | 3/2003 | Michaeli |
| 2008/0077023 A1 | 3/2008 | Campbell et al. |
| 2011/0160582 A1 | 6/2011 | Zheng et al. |
| 2012/0136240 A1* | 5/2012 | Pranevicius ....... A61B 5/02152 600/419 |
| 2015/0059448 A1 | 3/2015 | Shinno et al. |
| 2016/0000367 A1 | 1/2016 | Lyon |

\* cited by examiner

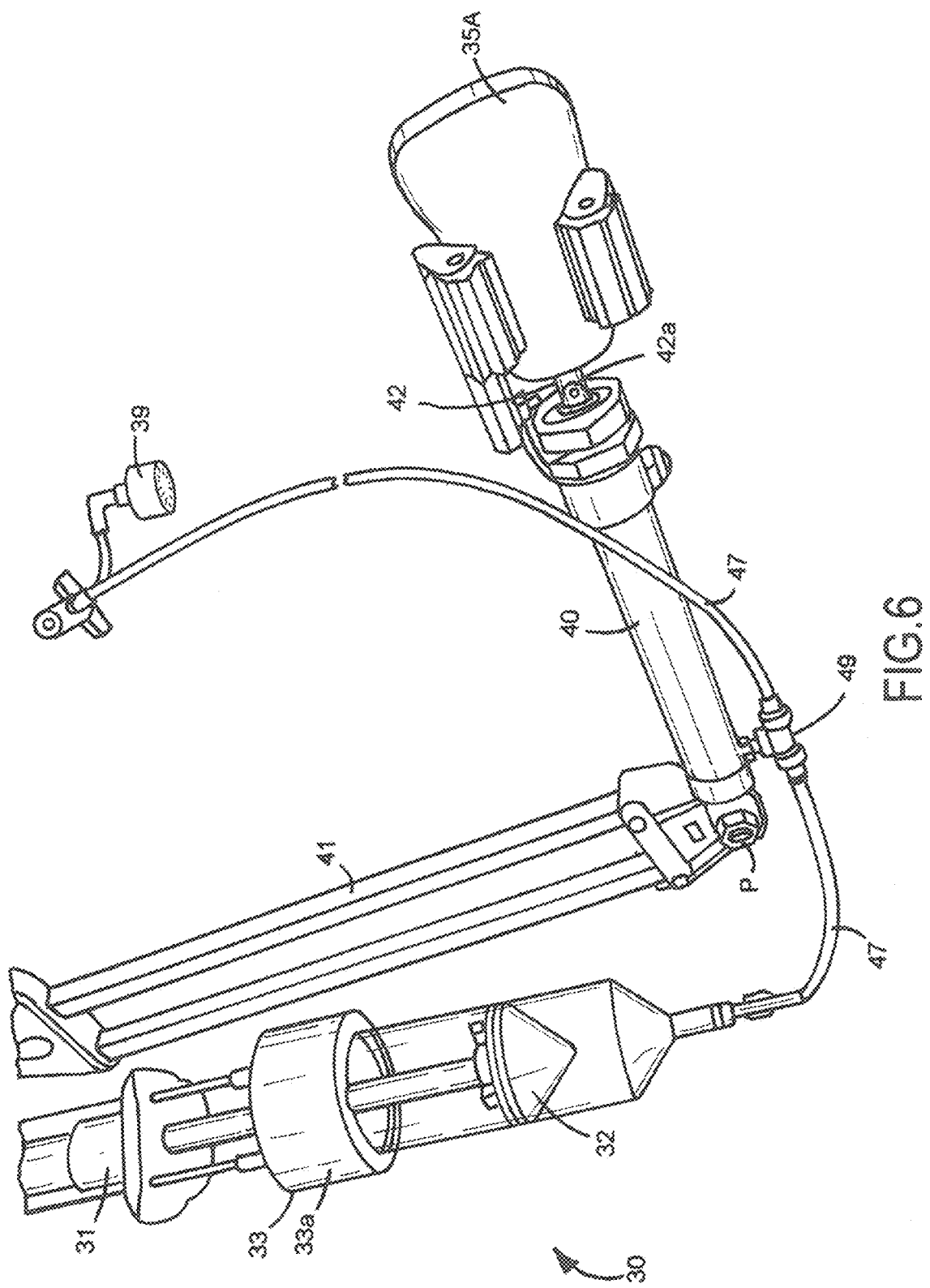

METHOD - 100

USING A MULTI-FREQUENCY ULTRASOUND PROBE, EMITTING AND RECEIVING ULTRASOUND WAVES INTO AND FROM A HEAD OF A SUBJECT SO AS TO PRODUCE A SIGNAL OF A PULSATION OF TISSUE OF A BRAIN OF THE SUBJECT DURING A TIME INTERVAL ⎯ 110

USING AN INSTRUMENT, NON-INVASIVELY APPLYING A PRESSURE TO A NECK OF THE SUBJECT TO EFFECTUATE A PARTIAL OCCLUSION OF AN INTERNAL JUGULAR VEIN OF THE SUBJECT, THE PARTIAL OCCLUSION STARTING AT A START TIME OF THE TIME INTERVAL, THE INSTRUMENT MEASURING THE PRESSURE AND INCLUDING A DISTAL ULTRASOUND PROBE CONFIGURED TO PRODUCE A SECOND SIGNAL FOR IMAGING THE INTERNAL JUGULAR VEIN ⎯ 120

USING A COMPUTER SYSTEM TO RECEIVE THE SIGNAL AND DERIVE FROM THE SIGNAL AN INTRACRANIAL PRESSURE WAVEFORM OF THE SUBJECT AND THE VOLUME VELOCITY OF THE INTERNAL JUGULAR VEIN, THE COMPUTER SYSTEM ALSO CONFIGURED TO RECEIVE AN OUTPUT OF THE START TIME AND TO MONITOR TIME FROM THE START TIME, THE COMPUTER SYSTEM ALSO CONFIGURED TO RECEIVE THE SECOND SIGNAL AND TO DERIVE FROM THE SECOND SIGNAL IMAGES OF THE INTERNAL JUGULAR VEIN ⎯ 130

DETERMINING, USING ONE OR MORE PROCESSORS OF THE COMPUTER SYSTEM, A LENGTH OF TIME (T) FROM THE START TIME TO A TIME WHEN THE INTRACRANIAL PRESSURE WAVEFORM IS SUFFICIENTLY COMPRESSED SO AS TO EXHIBIT A PREDEFINED DECLINE IN VARIABILITY ⎯ 140

FIG. 11

NON-INVASIVE DYNAMIC MEASUREMENT OF INTRACRANIAL RESERVE SPACE

FIELD AND BACKGROUND OF THE INVENTION

The present invention is in the field of medical diagnostic devices and methods. More particularly, the present invention aims to dynamically measure the intracranial reserve space noninvasively.

From the instant a patient with suspected brain injury arrives at the emergency room, a wide variety of complicated tests are obtained to help determine this damage. Clinical neurological investigations can be broadly classified in two ways: those that examine the anatomy of the brain (CAT scan and MRI) and those that examine the function of the brain (EEG, SPECT, and PET scan). Some of these are time-consuming and impractical for dynamic investigation such as repeating tests hourly or daily. While these diagnostic tools have advanced the understanding of the broad ranges of normative brain function, they disadvantageously rely on complex, expensive equipment that cannot be used continuously and near the bedside, and are available only in focal hospitals and not in peripheral medical clinics.

A CT scan, for instance, cannot be performed on a patient over and over within a period of 24 hours, or in some cases 6 hours, to determine anatomical deterioration in the brain, without subjecting the patient to dangerously mutagenic levels of radiation. It is also impractical to devote an expensive CT apparatus to repeated use on a single patient.

The "gold standard" to date for non-invasive measurement of the Intra Cranial Reserve Space (ICRS) is MRI Voxel Volumetry (MRIVV). However, MRIVV is expensive to purchase and to operate. It is also time consuming as the MRI scan is marked by hand, and cannot be used for wide clinical practices. It cannot be used repeatedly within a brief time frame such as minutes, hours, days or even a month, and cannot be used bedside. Interpretation of the results of the MRIVV usually requires a neuroradiologist to be present.

The need exists for an apparatus, preferably a portable bedside apparatus, that could be used repeatedly, for example within minutes or hours or days or months, and noninvasively on patients under observation for a suspected head injury or other neurological or neurosurgical condition, for example in order to ascertain whether anatomical deterioration has occurred over time.

SUMMARY OF THE INVENTION

One aspect of the present invention is a system for non-invasive monitoring of an intracranial reserve space (ICRS) parameter of a mammalian subject, comprising a multi-frequency at least two-dimensional ultrasound probe configured, beginning at a start time, to emit and receive ultrasound waves into and from a head of the subject and to produce a signal of intracranial brain tissue pulsations in at least a horizontal spatial and a vertical spatial dimension, the brain tissue pulsations responsive to pulses of a heart systole and/or arterial pressure; an instrument configured to non-invasively apply a pressure to effectuate a partial occlusion of an internal jugular vein of the subject, the partial occlusion starting at the start time, the instrument including a second ultrasound probe configured to produce a second signal for imaging the internal jugular vein; and a computer system configured to receive the signal and an output of the start time of the partial occlusion of the internal jugular vein of the subject, the computer system also configured, using one or more processors, to derive from the signal of intracranial brain tissue pulsations an intracranial brain tissue pulsation waveform based on at least three-dimensional pulsatility of the intracranial brain tissue, and to determine a length of time from the start time to a subsequent time at which the waveform is sufficiently compressed so as to exhibit a predefined decline in variability of at least 10%, the computer system also configured to receive the second signal and to derive from the second signal images of the internal jugular vein.

In some embodiments, the multi-frequency ultrasound probe emits in transmission mode at an emitter frequency and the probe receives at a receiver frequency such that the emitter frequency is lower than the receiver frequency.

In some embodiments, the instrument is configured to measure the pressure and wherein the instrument is configured to apply an initial pressure and subsequent greater pressures in uniform increments to the internal jugular vein.

In some embodiments, the instrument includes a motor or a compressor, at least one piston movable within a housing, and an applicator that includes the second ultrasound probe, a distal end of the applicator shaped to engage the neck of the subject.

In some embodiments, the multi-frequency ultrasound probe has a piezoelectric array configured to adapt to a shape of the skull.

In some embodiments, the multi-frequency ultrasound probe emits at a frequency of 0.5 to 3 MHz and receives at a frequency of 1.0 MHz to 6.0 MHz.

In some embodiments, an end of the multi-frequency ultrasound probe is shaped to conform to a skull and wherein the ultrasound probe emits at a frequency of about 1.0 MHz and receives at a frequency of up to 1.76 MHz using a carrier frequency of about 0.5 MHz to 1.76 MHz.

In some embodiments, variability of the waveform comprises at least one of the following parameters: (i) a variability of an amplitude of the waveform, (ii) a variability of an area under the curve of the waveform, (iii) a variability of a dominant frequency of the waveform (iv) a direction of high frequency shift of the waveform, (v) a phase shift of the waveform and (vi) a variability of a multiaxial spectroscopy of the waveform.

In some embodiments, the computer system is further configured to convert the signal into a dynamic image of a multiaxial pulsatility of brain tissue in at least a part of the head that the probe received ultrasound waves from.

In some embodiments, the computer system is configured to determine a suspicion that clinical deterioration of the subject is predicted to occur.

In some embodiments, the computer system is configured to predict at least one of (i) an elevated ICP of the subject and (ii) clinical deterioration of the subject, the prediction being derived from the determination of an intracranial reserve space (ICRS) parameter, wherein the ICRS parameter is at least one of (i) the length of time (T) and (ii) the intracranial reserve space (ICRS) capacity.

In some embodiments, the computer system is further configured to determine a magnitude of an intracranial reserve space (ICRS) parameter during the length of time (T).

In some embodiments, the computer system is configured to determine a magnitude of an ICRS capacity based on a volume velocity (V) of blocked venous blood output occluded at the IJV multiplied by the length of time (T).

In some embodiments, the computer system is configured to send an alert predicting at least one of (i) an elevated intracranial pressure and (ii) clinical deterioration of the subject.

In some embodiments, the computer system is configured to send an alert based on at least one of the length of time (T) and an intracranial reserve space capacity.

In some embodiments, the alert determines if the length of time is within a range of two to three seconds for a given pressure.

In some embodiments, the multi-frequency ultrasound probe is configured to receive ultrasound waves from at least two different intracranial locations.

In some embodiments, the two different intracranial locations are dissimilar according to predetermined criteria.

In some embodiments, the computer system is configured to determine a representative ICRS parameter from separate respective ICRS magnitudes at the at east two different intracranial locations.

In some embodiments, one or more processors of the computer system are configured to determine an ICRS parameter from a relationship of $\Delta V/\Delta P$.

In some embodiments, one or more processors of the computer system are configured to determine a suspicion that clinical deterioration either occurred or is predicted.

In some embodiments, the intracranial brain tissue pulsation waveform is provided by the computer system at a resolution of at least 6000 points per cycle.

In some embodiments, the computer system is also configured to derive a cross-sectional image of the IJV from the second signal and to determine an extent of partial occlusion of the IJV.

In some embodiments, the multi-frequency ultrasound probe is configured to operate in both a transmission mode and an impulse mode such that one of the (i) emitter and (ii) receiver operates in transmission mode and another of the (i) emitter and (ii) receiver operates in impulse mode.

In some embodiments, the computer system is configured to determine a further length of time beginning from the time at which the waveform is sufficiently compressed so as to exhibit the predefined decline in variability to a normalization time at which the predefined decline in variability has been reversed, the reversal such that a variability of the waveform at the normalization time equals, within a predefined degree of accuracy, a variability of the waveform at the start time. In some embodiments, the computer system is configured to send an alert predicting future clinical deterioration of the subject if the further length of time is excessive or too short relative an expected normal further length of time.

In some embodiments, the system further comprises a display forming part of or connected to the computer system, the display configured to dynamically display the intracranial pressure waveform so as to visually depict the variability of said waveform.

In some embodiments, the multi-frequency ultrasound probe, the second ultrasound probe and the one or more processors work synchronously.

Another aspect of the present invention is a method of non-invasively monitoring intracranial reserve space (ICRS) parameter of a mammalian subject, comprising using an at least two-dimensional multi-frequency ultrasound probe, emitting and receiving ultrasound waves into and from a head of a subject so as to produce a signal of intracranial brain tissue pulsations of the subject during a time interval in at least a horizontal spatial and a vertical spatial dimension, the brain tissue pulsations responsive to pulses of a heart systole and/or arterial pressure; using an instrument, non-invasively applying a pressure to a neck of the subject to effectuate a partial occlusion of an internal jugular vein of the subject, the partial occlusion starting at a start time of the time interval, the instrument measuring the pressure and including a distal ultrasound probe configured to produce a second signal for imaging the internal jugular vein; using a computer system to receive the signal and derive from the signal an intracranial brain tissue pulsation waveform of the subject and the volume velocity of the internal jugular vein, the computer system also configured to receive an output of the start time and to monitor time from the start time, the computer system also configured to receive the second signal and to derive from the second signal images of the internal jugular vein; and determining, using one or more processors of the computer system, a length of time (T) from the start time to a time when the intracranial brain tissue pulsation waveform is sufficiently compressed so as to exhibit a predefined decline in variability of at least 10%.

In some embodiments, the method further comprises the multi-frequency ultrasound probe emitting in transmission mode at an emitter frequency and the probe receiving at a receiver frequency such that the emitter frequency is lower than the receiver frequency.

In some embodiments, the variability of the waveform comprises at least one of the following parameters: (i) a variability of an amplitude of the waveform and (ii) a variability of an area under the curve of the waveform, (iii) a variability of a dominant a frequency of the waveform (iv) a direction of high frequency shift of the waveform, (v) a phase shift of the waveform and (vi) a variability of a multiaxial spectroscopy of the waveform.

In some embodiments, the method further comprises converting the signal into a dynamic image of a multiaxial pulsatility of brain tissue in a sector of the head from which the multi-frequency ultrasound probe received ultrasound waves.

In sortie embodiments, the method further comprises having the multi-frequency ultrasound probe emits at between 0.5 and 1.1 MHz and receives at between 1.0 and 2.2 MHz using a carrier frequency of 0.5 to 2.2 MHz.

In some embodiments, the method further comprises applying the pressure by applying an initial pressure and then increasing the pressure from the initial pressure stepwise in uniform increments until the predefined decline in variability of the ICP waveform occurs.

In some embodiments, the method further comprises determining that the subject has an abnormal intracranial reserve space and that clinical deterioration is either predicted to occur or inferred to have occurred.

In some embodiments, the method further comprises determining, using the one or more processors, a magnitude or a relative magnitude of an intracranial reserve space (ICRS) parameter given the pressure applied for the length of time (T).

In some embodiments, the method further comprises determining the magnitude of the ICRS parameter using a relationship of a volume velocity (V) of venous blood output occluded at the internal jugular vein for a given pressure (P) taking into consideration the length of time (T) of application of the pressure, and wherein the ultrasound Doppler outputs the linear velocity and cross-sectional diameter of the internal jugular vein. In some embodiments, the method further comprises determining that a further medical action is needed if the length of time (T) is less than a predefined length of time for a given pressure applied to the subject to effectuate the partial occlusion, wherein the predefined length of time has a specific length that is at least 2 seconds and not more than 3 seconds.

In some embodiments, the method further comprises determining an intracranial pressure from the pressure applied to the subject at a time when the intracranial brain tissue pulsation waveform begins to decline in variability.

In some embodiments, the method further comprises monitoring the ICRS parameter dynamically.

In some embodiments, the method further comprises applying the pressure to the internal jugular vein for between 3 and 25 seconds so as to partially occlude 5% to 25% of a cross-section of the internal jugular vein.

In some embodiments, the method further comprises applying the pressure to the internal jugular vein for between 3 and 10 seconds so as to partially occlude 5% to 15% of a cross-section of the internal jugular vein.

In some embodiments, the method further comprises repeating the method at least once so as to determine a subsequent length of time (T), and predicting at least one of elevated ICP and clinical deterioration, if the subsequent length of time (T) is less than the length of time (T) by a predefined amount.

A further aspect of the present invention is a system for non-invasive monitoring of an intracranial reserve space (ICRS) parameter of a mammalian subject, comprising: a multi-frequency ultrasound probe configured, beginning at a start time, to emit and receive ultrasound waves into and from a head of the subject and to produce a signal of brain tissue pulsation; an instrument configured to non-invasively apply a pressure to effectuate a partial occlusion of a cross-section of an internal jugular vein of the subject, the partial occlusion starting at the start time, the instrument including a second ultrasound probe configured to produce a second signal for imaging a cross-section of the internal jugular vein, the second ultrasound probe having a Doppler ultrasound output for measuring a linear velocity of venous blood at the internal jugular vein; and a computer system configured to receive the signal and an output of the start time of the partial occlusion of the internal jugular vein of the subject, the computer system also configured to receive the second signal and to derive from the second signal an image of the cross-section of the internal jugular vein and to determine the linear velocity of venous blood at the internal jugular vein, the computer system also configured, using one or more processors, to derive from the signal an intracranial brain tissue pulsation waveform, and to determine an ICRS capacity from (i) a length of time (T) from the start time to a subsequent time at which the waveform is sufficiently compressed so as to exhibit a predefined decline in variability of at least 10% and from (ii) a volume velocity (V) of blocked venous blood output occluded at the IJV, wherein the volume velocity is determined by the computer system from the linear velocity of the internal jugular vein derived from the Doppler ultrasound output and from the image of the cross-section of the internal jugular vein.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1Ca is a schematic view of an alternative embodiment for utilizing springs with piezoelectric crystals for the distal end of an ultrasound probe, in accordance with one embodiment of the present invention;

FIG. 6 is a perspective view of a pressure application and measuring instrument and holder, in accordance with one embodiment of the present invention;

FIG. 11 is a flow chart showing a method of the present invention in accordance with one embodiment of the present invention.

DETAILED DESCRIPTION OF THE INVENTION

Figure 1A:
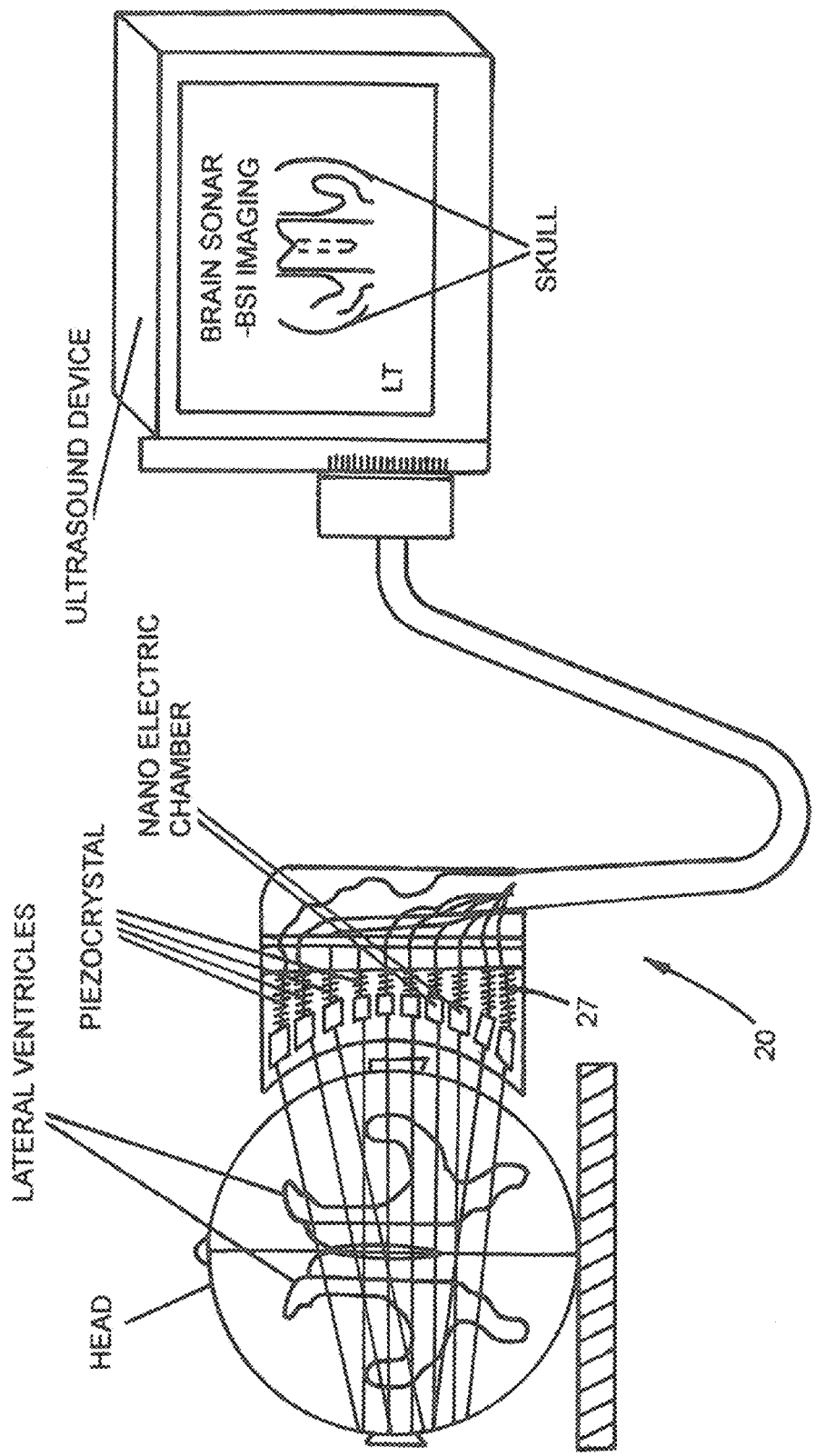
FIG. 1A is a vertical side view of an ultrasound probe, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Intracranial reserve space is an anatomical phenomenon describing the volume of intracranial space filled with cerebral spinal fluid (CSF). As used in this patent application, the term "intracranial reserve space" "ICRS" refers to all spaces within the cranium that would normally be filled with cerebral spinal fluid when the subject is healthy. This includes convexital ICRS, brain's basal surface ICRS, including basal cisterns and intracerebral ICRS, i.e. brain's ventricles. ICRS is therefore not limited to the convexital surface and subarachnoid space around the brain, but also includes the ventricles, cisterns and sulci that the CSF normally fills when the patient is healthy. However, the ICRS capacity as used herein is not the actual true volume of the total ICRS as defined above but is rather merely the available capacity of the ICRS until the ICRS is deemed "occupied", either as a result of implementing the present invention by blocking venous blood from exiting the cranium, or as a result of an abnormality such as a SOL (space occupying lesion). The ICRS is deemed "occupied" by the present invention when the ICP waveform amplitude (or other selected variability parameter of the ICP waveform) compress to the point of being flattened. It is noted that although the CSF inside the ICRS is a liquid and as such is incompressible, the "occupying" of the ICRS by either (i) extra venous blood blocked from exiting through the internal jugular vein or by (ii) a SOL, causes the CSF to be "pushed out" of the ICRS and to exit the cranium into the spinal canal. However, due to the space limitations of the spinal canal, only a small portion, approximately 5-10 cc out of 70-80 cc, of the CSF exits into the spinal canal before the ICRS is considered "occupied" and the amplitude or other variability indicator of the ICP waves flatten. "ICRS capacity" is the capacity, in volume, that the ICRS can hold from the extra volume of intracranial blood that is blocked from exiting the cranium after partial occlusion of the IJV until the variability (for example amplitude) of brain tissue pulsations declines by a predefined level. Accordingly, the "ICRS capacity" as used herein is not the actual true volume of the total ICRS but is rather merely the available capacity of the ICRS (for example to hold extra venous blood) before the variability parameter such as amplitude of the ICP waves flatten (as defined quantitatively) and the ICRS is deemed "occupied". The ICRS is deemed "occupied" when the ICP wave amplitude (or other selected variability parameter of the ICP waves) compress to the point of being flattened (as defined by the user preferably quantitatively, or in other embodiments visually).

The present invention generally provides a portable inexpensive device/system and method configured to noninvasively measure, in some embodiments to non-invasively measure repeatedly, an ICRS parameter such as the time to occupy the ICRS or the volume capacity of the ICRS by examining the brain tissue multidimensional pulsatile activity noninvasively using ultrasound waves. The device is highly accurate and has high resolution. It is believed that soft tissues and fluid compartments exhibit their own characteristic resonant responses to heart systolic and arterial pressure pulses radiating through the tissues of the body (input signal). When a target tissue is stimulated by specific ultrasound signals, the nature of the reflected ultrasound energy waves that bounce back from the tissue depends on the resonant state of the tissue (output signal). The pulsatile pattern of resonance responses of a tissue to specific ultrasome stimulation is then collected and interpreted through specific mathematical algorithms to provide information about the physiological properties of the tissue. The device, method and system provides a dynamic high accuracy and high resolution technique for intracranial reserve space parameter measurement in some embodiments using ultrasound pulsatility and a skull shape adjustable ultrasome dual frequency probes, for example needle-like dimensional array of piezocrystals lying on a rectangle strip shape and operating on different, relatively low, transmitting frequency and receiving frequency mode. Reflected ultrasome energy is converted accurately to signals providing data corresponding to noninvasive dynamic, multiaxial pulsatility activity, intracranial reserve space and in some embodiments intracranial pressure (ICP) in the preselected volume of tissue.

Some non-limiting advantages of certain embodiments of the present invention include its high resolution and accuracy, being portable, noninvasive, dynamic (i.e. can be repeated within relatively short time intervals such as an hour or even 10 minutes or less), inexpensive, and utilizing easy to operate instruments. It has the ability to measure the intracranial reserve space and determine quantitatively the physiological status of any brain tissues or fluid compartments even before elevation of the ICP level occurs in some embodiments. Thus, reduction of ICRS is useful as a preventive measure and allows new additional and recurrent investigation of patient and preventive treatments. Additional modalities are available for degree of occupation ICRS and prevention of future ICP elevation. The present invention, in certain embodiments, detects a significant change, for example loss, of capacity (volume) of the intracranial reserve space (ICRS) ("ICRS capacity"), which is most commonly seen from swelling or a growth associated with a contusion, a cranial tumor a stroke. If these conditions are left unchecked, they may be fatal. A loss of ICRS volume can occur within minutes or hours.

Further, spectral data (i.e. ultrasound cerebral pulsatile spectroscopy-USCPS) can be easily obtained to provide additional information on the tissue composition and structure. The versatility of the present invention allows it to be used to aid in diagnosis and provide information to direct the most appropriate course of therapy such as in unilateral traumatic contusions, intracranial hemorrhages, brain tumors, cerebral vascular accidents (CVAs), etc.

In a broad embodiment, the present invention is a medical diagnostic tool based on ultrasound waves that has the capability to generate important diagnostic information non-invasively and dynamically about the physiological status of virtually any fluid space, tissue, or organ of interest tissues anywhere in the body including within the brain volume, intra-abdominal pressure (IAP), and intra-urinary bladder pressure (IUBP).

Prior art methods for ultrasome viewing of human tissue, typically utilize ultrasound pulses of one dimension, which are limited in the ultrasound intensity (allowable by government regulation) to be approximately 120 mW per $cm^2$.

This was thought to be the only appropriate ultrasome properties for penetrating the skull, and it was thought that two dimensional ultrasound could not penetrate the adult human skull due to considerable ultrasound power attenuation at the high frequencies (over 3 MHZ). In contrast, the present invention now suggests use of two or three dimensional ultrasound, which can be used to penetrate the skull for example at the intensity of 40-100 MiliW/per cm$^2$, which is the new FDA regulatory requirement for intensity. The three-dimensional pulsations of brain tissue that are output in some embodiments of the present invention improve over the imaging of U.S. Pat. No. 6,328,694 by the present inventor also in that the imaging in the '694 patent is derived from only vertical pulsatility, whereas in the present invention the tissue pulsatility is generated in accordance with some embodiments from each multi-axial direction, including even oblique directions in some embodiments. This provides more data and more accurate imaging.

In still further contrast to the prior art, in some embodiments, as a result of use of dual frequencies of the ultrasound probe 20 applied to the head, so that in transmission mode the emitter uses a lower frequency and the receiver uses a higher frequency, one obtains greater depth of penetration of the ultrasound waves. In addition, this reduces black noise and improves ultrasound spatial and image resolution and quality. This transmission mode (parallel, continuous mode of the ultrasound beam) of ultrasound investigation causes activation of different anatomical targets of brain and these activated targets generate new multi-frequency intracranial ultrasound beams which are distributed in multiple directions within the intracranial cavity. The reflected beams and integrative recordings and stratification of the two different kinds of beams achieve much better image quality, elevated coefficient signal/noise ratio and improved quality of resolution and imaging. Specifically, this achieves receipt of much clearer images of the brain for evaluating the brain's midline shift and the size of brain ventricles and this provides better temporal resolution of multiaxial brain pulsatility and spectral analysis. In further contrast to the prior art, for example transcranial Doppler (TCD), which requires, and is dependent on, the expertise of the operator who operates the system, and in contrast to other prior art methods and devices requiring significant experience to interpret the results, the claimed invention is not dependent on such operator expertise and consequently the accuracy of the resulting measurements is not dependent on the operator's expertise, once the operator has been trained to use the present invention. For example, determination of the compression of the ICP waveform to a predefined degree can in some embodiments be determined by the computer system using software such as special purpose software. In further contrast to the prior art such as TCD and other prior art methods, which depend on the professional evaluation of the results and/or require complicated algorithms to interpret the results, the claimed invention is not dependent on professional evaluation of the results. Even if in certain embodiments one utilizes a visual observance by the user that there has been a partial occlusion of the IJV as seen from the imaging of the IJV, or that the variability of the amplitude of the ICP waveform has flattened, that is a clear visual determination that the operator can make quickly without extensive interpretation. In further contrast to the prior art methods and devices for measuring and monitoring the ICRS, such as MRI and CT, which require large and expensive equipment in a hospital or clinic, the present invention in certain embodiments is a portable bedside apparatus that non-invasively and dynamically measures and monitors the intracranial reserve space (ICRS) of a patient, and in a typical case, a technician or nurse or even a layman can be trained to use it. In some embodiments this training can be completed in several hours.

For a suspected head injury, the present invention is able in certain embodiments to detect a significant loss of volume of the ICRS for example from swelling associated with a contusion, a cranial tumor or a stroke, which if left unchecked may be fatal. Occupation of the patient's ICRS volume can occur within minutes. Monitoring ICRS and ICP in ER rooms may well dramatically improve neurosurgery by allowing earlier detection and diagnosis of space occupying lesions. In certain embodiments, the present invention is also helpful in treatment of other neurological conditions including stroke, brain tumors, impaired consciousness, hydrocephalus, central nervous system diseases and intracranial injury. Knowing the ICRS and ICP non-invasively and dynamically is useful to determining the course of treatment for numerous conditions of the brain and head. For example, different treatments are provided to patients with elevated ICP than patients with lower ICP.

In still further contrast to prior art methods of measuring ICRS, which require a neuroradiologist to be present personally, the method and device of the present invention can be implemented by a technician or others trained in its use. In further contrast to prior art non-invasive methods, which cannot be used dynamically, the present invention can be used dynamically, i.e. repeated within days, hours or even minutes. This means the measurements can be repeated after a relatively short amount of time, much shorter than for a brain MRI (or for a brain CT). Dynamic, non-invasive monitoring of ICRS parameters (such as the length of time it takes for the ICRS to become "occupied" or the available volume or capacity of the ICRS) opens up the possibility of treating patients before ICP elevation or clinical deterioration occurs and in some cases before 80% occupation of ICRS occurs. MRI, for example, is not available to be used dynamically (repeated use during short intervals of minutes or hours or days), and is expensive and time consuming. MRI and CT cannot be used continually or be available near the bedside, and are available only in focal hospitals and not in peripheral medical clinics. Due to these disadvantages, CT and MRI are impractical for wide clinical use for non invasive measurement and dynamical monitoring of ICRS parameters. A CT scan is also too dangerous for repeated use. Today, not everyone who needs an MRI receives it. But if ICRS monitoring already pointed to a reduced or an elevated ICP, the MRI or CT would be justifiably given and treatment could be advanced. If even a patient with a headache were shown to have a much smaller than expected ICRS, a CT or MRI would be run and if it showed a SOL growth, emergency surgery could be considered. This could allow surgery at an earlier stage prior to clinical deterioration thus improving the expected outcome of neurosurgical interventions, which is highly dependent on the health of the patient.

If a patient has a Space Occupying Lesion (SOL), such as an intracerebral hemorrhage (ICH), a brain tumor, a brain contusion or brain swelling, these lesions do not immediately result in an elevated intracranial pressure (ICP). For example, a space occupying lesion (SOL) may progress through multiple stages as follows: during the first stage, the lesion begins occupying the nearest convexital ICRS. Further growth of the SOL during a 2 nd stage may cause depression of the walls of the ventricles of the brain experience and ventricular asymmetry. The 3rd stage is depression of basal cisterns. The fourth stage is a shift of 2 to 5 mm in the brain's midline, called BMLS. The fifth stage is a BMLS of 5-10 mm and the 6$^{th}$ stage is a BMLS of 10-15 mm or more.

It is important to note that during the first four stages of the growth of a space occupying lesion (SOL), clinical signs are very difficult to obtain and symptoms of disease are very difficult to discern. Although a patient may have a large-sized SOL as a result of stages 1-4 of SOL growth, compensatory mechanisms of ICRS, namely the ICRS volume and cerebral spinal fluid (CSF) outflow front the head, may prevent clinical manifestation of signs of ICRS occupation and elevated intracranial pressure (ICP). This is especially true of elderly patients who have elevated ICRS capacity since during aging, ICRS grows due to central and peripheral brain tissue atrophy. Accordingly, dynamic evaluation of ICRS and changes in ICRS, may provide crucial information even before manifestation of ICP elevation. ICRS parameters such as the extent of reduction in the volume of ICRS, for example from a SOL, or the length of time until ICRS is occupied (as defined by variability declining by a predefined amount) by partial occlusion of the IJV for example, are good predictors of neurological developments of the patient, before clinical deterioration, and has significant prognostic value in neurosurgery. Specifically, reduction of ICRS may well indicate that in the near future the patient will develop an elevated ICP and/or will experience clinical-neurological deterioration, something the prior art does not achieve. Consequently, ICRS monitoring may well be a more sensitive marker than ICP monitoring for patients with acute and chronic SOL growth. ICP elevation occurs after ICRS occupation and patients with ICP elevation already have experienced significant clinical deterioration requiring immediate surgical intervention. Furthermore, a significant reduction of the patient's ICRS within a short time interval is an indicator justifying recurrent CT investigation. Even without clinical-neurological deterioration, dynamic monitoring of ICRS is an important additional tool for neurologists and neurosurgeons justifying repeating a CT, even when the previous CT occurred 10-15 minutes ago, something that normally would not be allowed under CT guidelines. The repeated CT can also save previous time consumed by discussions between radiologists and other colleagues as to whether to repeat a CT.

Note that in contrast to reduction of ICRS from a first measurement to a second measurement (especially in a relatively short time interval) which may well indicate future elevated ICP or clinical deterioration, in adults, if based on a single measurement the ICRS is found to be high (based on length of time (T) or based on absolute ICRS capacity), this alone would indicate that intracranial pressure is likely to be low or normal and conversely, if the ICRS is found to be low (based on length of time (T) or based on absolute ICRS capacity) in a single, measurement, it indicates that intracranial pressure is likely to be high or normal. In further contrast to prior art techniques, certain embodiments of the present invention may also be useful as a general check-up for healthy individuals. For example, a CVA (stroke) is common among the elderly and can be prevented in high-risk patients or can be efficiently treated if detected in a timely manner. As a bedside noninvasive apparatus which does not involve high levels of radiation, the apparatus of the present invention can be used to perform routine preventative screening on the elderly.

The principles and operation of a Non-Invasive Dynamic Measurement of Intracranial Reserve Space according to the present invention may be better understood with reference to the drawings and the accompanying description.

In this patent application, the term "intracranial brain tissue pulsation waveform" or "ICP waveform" refers to the wave function that is obtained, and in some embodiments displayed, when the signal from the ultrasound probe placed on the subject's head (in some embodiments in both a horizontal position and in a vertical position) is adapted by software 55, such as special purpose software 55, of the computer system 50 of the present invention to show real time images of brain tissue pulsation. For example, the ultrasound probe 20 provides brain pulsations, such as two-dimensional brain pulsations, that are adapted by software, i.e. in some embodiments by first applying the fast fourier transform (FFT) and then applying the inverse fast fourier transform (IFFT), to yield two-dimensional pulsatility which in some embodiments is further converted to three-dimensional pulsatility by including signals from both horizontal and vertical positions held by the probe. The additional dimensions provide more information and more accurately capture the brain tissue and its real-time movements. For example, intracranial pressure and intracranial reserve space are more precise by using both dimensions since horizontal pulsations may be more informative both for ICP and for the compression of the waveform used for ICRS. Multi-dimensionality, i.e. even further dimensions such as oblique directions, may be included utilizing computer science. Accordingly, the intracranial brain tissue pulsation waveform used in the present invention takes into account brain tissue pulsations, arterial blood flow input and venous blood flow output. In some embodiments, it also takes into account cerebral spinal fluid (CSF) outflow.

"ICP waves" refers to the waves of the ICP waveform.

Referring now to FIGS. 1 through 3, there are shown an example of a system for observing ICRS in a volume of tissue in a subject in accordance with one embodiment of the present invention.

Figure 2A:
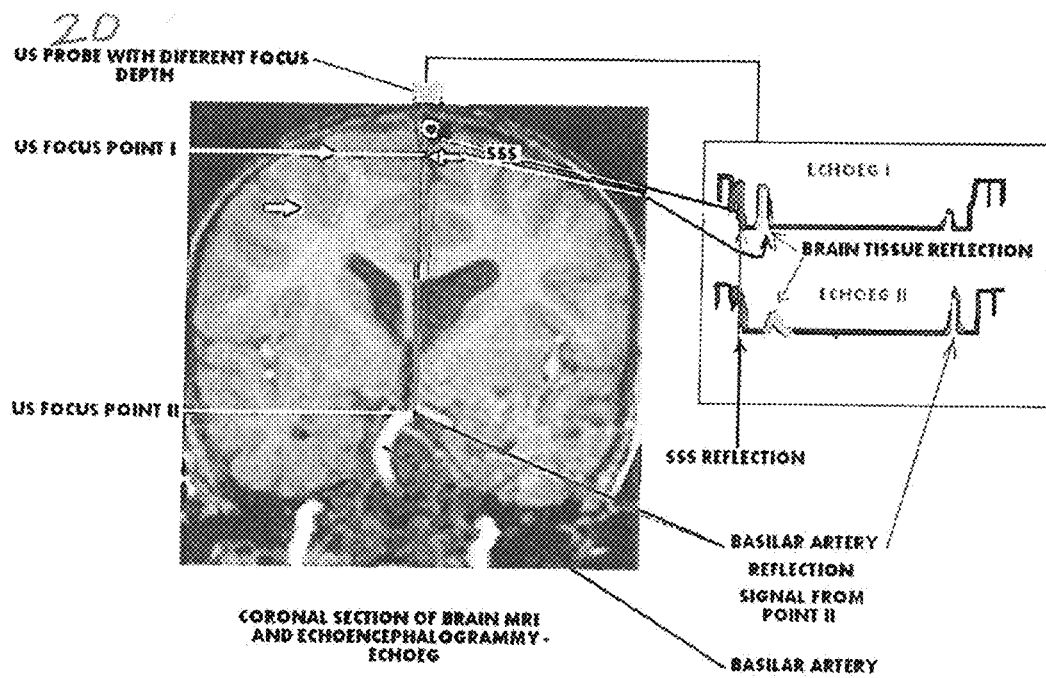
FIG. 2A is a coronal sectional view of brain MRI and on the right an echo encephalogram showing the real-time pattern of brain pulsation from ultrasound imaging using a one-dimensional A mode ultrasound probe from which it is possible to derive ICP waveform, wherein SSS refers to Superior Sagittal Sinus, in accordance with one embodiment of the present invention.

FIG. 2A shows on the left a brain MRI to help visualize where the ultrasound reflections come from. The right side of FIG. 2 shows an echo encephalogram with real-time pattern of brain pulsation from ultrasound imaging using a one-dimensional A mode ultrasound probe. It is possible using the computer system of the present invention to derive ICP waveform directly from the one-dimensional signal on the right of FIG. 2A. This is less expensive that a two-dimensional ultrasound probe 20. However, it is also less accurate since it is derived from a one-dimensional probe and also because it is not derived from an image.

Figure 2B:
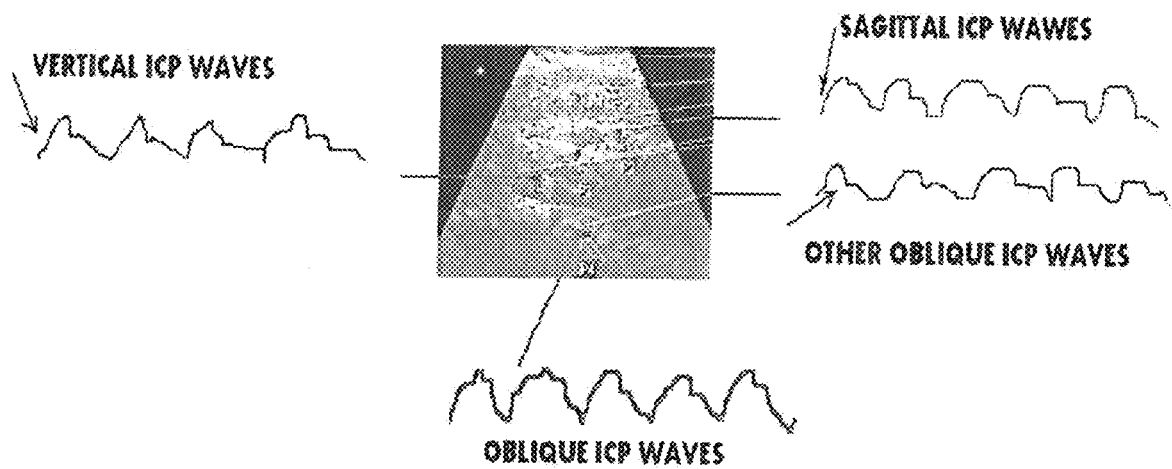
FIG. 2B is a further sectional view showing in the middle of the figure the real-time image of multi-dimensional brain tissue pulsation from two-dimensional ultrasound sector imaging and on the left and right TCP waveform derived from the image, in accordance with one embodiment of the present invention.

FIG. 2B shows a sectional view in the middle of the figure having a real-time image of multi-dimensional brain tissue pulsation from a two-dimensional ultrasound sector imaging probe 20. On the left of FIG. 2B and on the right of FIG. 2B are ICP waveforms derived from the image in the middle. Although more expensive, these ICP waveforms are more accurate because they derive from an image and because they derive from a two-dimensional ultrasound probe. Both the graph on the right of FIG. 2A and the graphs on the left and right of FIG. 2B represent the reflected ultrasound energy which is detected from a selected pixel in the tissue at different depths and exhibit the pulsatile activity (differential between emitted and reflected ultrasound energy—brain tissue's ultrasound energy shift) as a function of time. As shown, some observation of pulsatile activity will vary with orientation or direction of the observations.

In a healthy individual, it takes time, for example about 3 seconds (depending upon age and other factors) for the intracranial reserve space to be occupied by the blockage of blood outflow to the IJV. In a patient with some of the ICRS already occupied by a pathological growth, the time to "occupy" the ICRS by the extra blood would be significantly less.

The time interval for occupying the ICRS after partial occlusion of the IJV is a measure of how long it takes to "occupy" the intracranial reserve space from when the mild pressure applied at the neck of the subject on the IJV causes the partial blockage of blood outflow out of the cranium. For a normal adult, taking into consideration age and if desired other suitable factors, it takes about 3 seconds to "occupy" the intracranial reserve space when the blood flow out of the brain is affected by partially occluding the IJV. If the subject's intracranial reserve space instead took only one second to become "occupied", for example, it could indicate growth of an SOL within the cranium that had reduced the volume of the ICRS already before the partial occlusion of the IJV. If on the other hand it took too long, for example 7 seconds, that could indicate that the intracranial reserve space was too large. If at took 2 seconds for the ICRS to become "occupied", the measurement is repeated, at least according to one embodiment. If the ICRS is found to be constant based on receiving similar results from multiple measurements, then the deviation from 3 seconds is small enough, for example 2 seconds or 4 seconds, then the subject may be considered to not be in danger. This conclusion is only one non-limiting example of a medical conclusion that may be made from the additional useful information provided by the present invention.

Figure 3A:
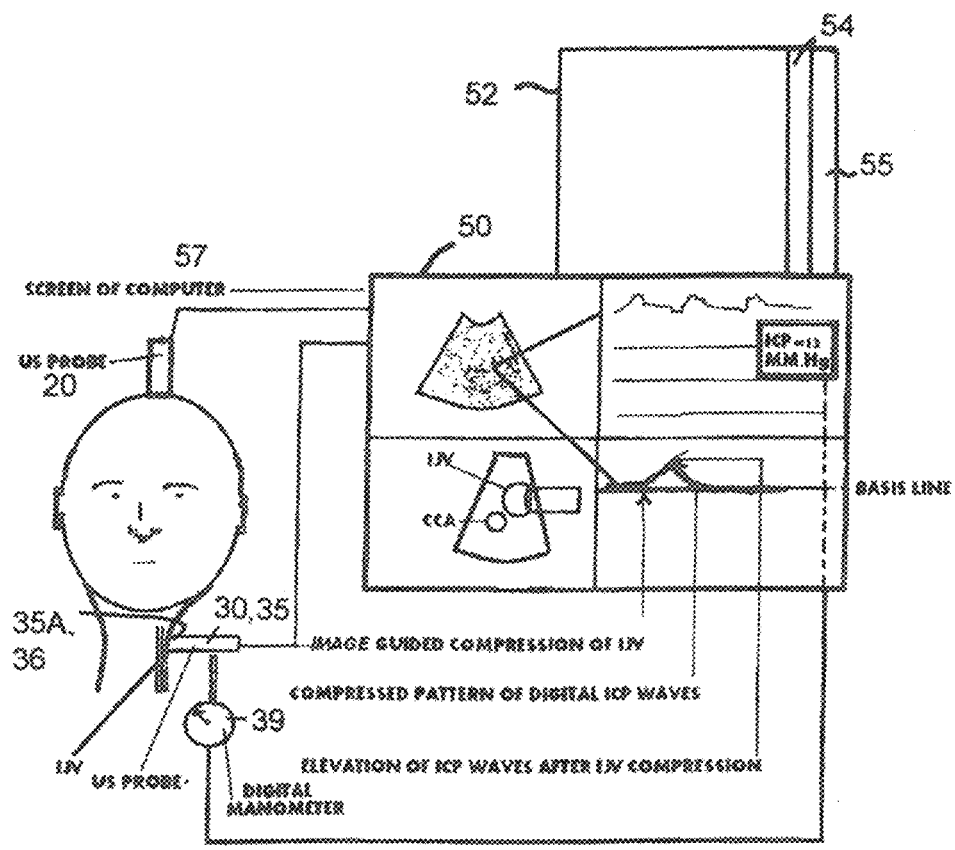
FIG. 3A is a schematic view of a system for noninvasive ICRS and ICP monitoring with image guided internal jugular vein (IJV) cross-sectional compression and showing nearby the cervical portion of the internal carotid artery (ICA), in accordance with one embodiment of the present invention.

Referring now to FIG. 3A, there is shown a non-invasive measurement of the ICP as well as non-invasive measurement of amplitude of ICP waveform compression of brain tissue pulsation which is guided by images of partial occlusion of the internal jugular vein (IJV). Stepwise partial occlusion of IJV is performed for example on a supine patient in accordance with one embodiment of the present invention, under guidance of 2D-ultrasound imaging. In some embodiments, the jugular vein probe 35A emits ultrasome frequency within the range from 3.5 MHz to 24 MHz. In some embodiments, the device includes a stepper motor, and on the opposing side, a digital manometer to determine how much pressure was placed on the IJV.

As shown in FIG. 3A, the present invention is in certain embodiments a system for monitoring intracranial reserve space. FIG. 3A shows one embodiment of the system 10 of the present invention including a display screen 57 (forming part of the computer system 50) upon which is shown side by side: the ultrasound reading taken from the IJV probe 35A; pulsatile views of the cranium from the probe 20 including an externally placed cranial location marker; a compressional ICP waveform graph showing the minimal/maximal amplitude (or other waveform parameter) of the ICP waveform.

System 10 includes in some embodiments an ultrasound probe 20 for application to the cranium, an instrument 30 for applying pressure to the neck of the subject and a computer system 50 for processing signals generated by the ultrasound probe 20 and for determining, an intracranial reserve parameter. In some embodiments, the ICRS parameter is an ICRS capacity measuring an absolute volume as determined by the volume of velocity of venous blood outflow blocked multiplied by the length of time (as described below) from a partial occlusion of the IJV until the ICP waveform compresses to a predefined extent as measured by a decline in its variability and further adjusted by multiplying by a percentage of the cross-section of the IJV that has been partially occluded. In other embodiments, the ICRS parameter is a length of time determined by a calculation made by the computer system 50.

In certain embodiments, system 10 for non-invasive monitoring of an intracranial reserve space (ICRS) parameter of a mammalian subject, comprises an ultrasound probe 20, such as a multi-frequency ultrasound probe 20, that is configured, beginning at a start time, to emit and receive ultrasound waves into and from a head of the subject and to produce a signal corresponding to brain tissue pulsation. System 10 in some embodiments also includes an instrument 30 configured to non-invasively apply a pressure to effectuate a partial occlusion (or a deformation of the walls) of an internal jugular vein of the subject, the partial occlusion starting t the start time. The instrument 30 also includes in some embodiments a second probe 35A (called "second" only in the sense that probe 20 is the first probe), such as an ultrasound probe, configured to produce a second signal from which computer system 50 derives images, for imaging the internal jugular vein to see when the partial occlusion started. The imaging by the computer system is for example for imaging a cross-section of the internal jugular vein, or for imaging another view of the internal jugular vein that allows the cross-section (or in other embodiments allows the diameter (or even some other parameter of the IJV sufficient to reveal when the partial occlusion starts)) of the internal jugular vein to be monitored to see when the partial occlusion has started. The jugular vein probe 35A emits and receives at a frequency within the range of 3.5 MHz to 24 MHz, according to certain embodiments. The emitting frequency may be the same as the receiver frequency in the case of the jugular vein probe 35A.

When the partial occlusion has been determined to have started, in some embodiments the user can push a timer. Alternatively, the computer system 50 can determine when the partial occlusion of the IJV has occurred (because the computer system 50 is also configured to receive the second signal and to derive from the second signal images of the internal jugular vein) and automatically start the timing function. In some embodiments, the computer system 50 simply records the time or the amount of time, such as seconds or milliseconds elapsed, throughout beginning when the partial occlusion starts. These are non-limiting ways of measuring the length of time (T), as defined below.

System 10 in some embodiments also includes a computer system 50 configured with all suitable hardware and software necessary to receive the signal from the ultrasound probe 20 configured for the subject's skull 11 and to receive an output of a start time of the partial occlusion of the internal jugular vein of the subject. Computer system 50 in some embodiments is also configured, for example using one or more processors 52 and software 55, such as special purpose software 55, and all suitable and necessary hardware and software including memory storage 54, to derive from the signal an intracranial brain tissue pulsation waveform, and to monitor time so as to determine a length of time from the start time to a subsequent time at which the waveform is sufficiently compressed so as to exhibit a predefined decline in variability. The software 55 for deriving the intracranial brain tissue pulsation waveform from the signal of the ultrasound probe 20 is known or readily adaptable from known software associated with single or two-dimensional ultrasound probes. Computer system 50 also includes in some embodiments all suitable hardware and software for displaying brain tissue pulsatility, such as the ultrasound device shown in FIG. 1A.

"Deriving" the ICP waveform from the signal of probe 20 includes deriving it directly and includes deriving the ICP waveform from the signal indirectly. In one embodiment, computer system 50 indirectly derives the ICP waveform from the signal generated by probe 20 by deriving the ICP waveform from an image of brain tissue pulsation wherein the image of brain tissue pulsation had been derived from the signal generated by probe 20. In a different embodiment, computer system 50 directly derives the ICP waveform from the signal generated by probe 20, which typically is a two-dimensional probe 20 but can also be a one-dimensional probe 20.

Figure 9:
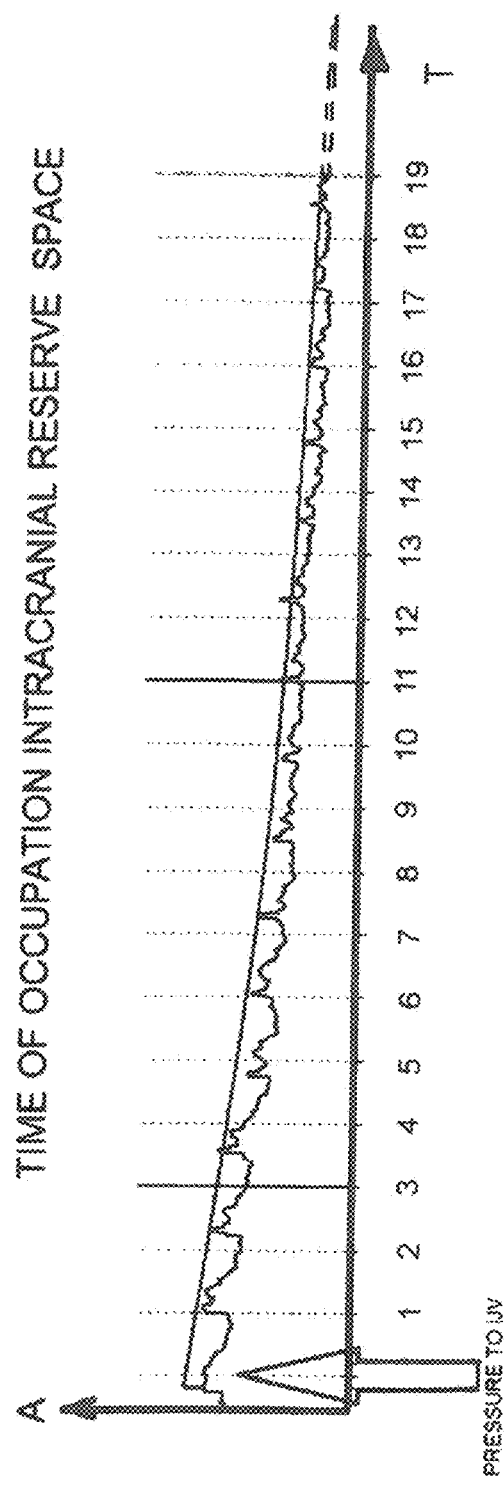
FIG. 9 is a graph of ICP waveform amplitude of a patient from a time in seconds of pressure applied to the IJV until compression of variability of ICP waveform, in accordance with one embodiment of the present invention.

FIG. 9 shows an intracranial brain tissue pulsation waveform starting with a certain variability in amplitude, beginning to compress or flatten and continuing until the variability, as measured in terms of amplitude, is compressed after 19 seconds. In some embodiments, certain portions of computer system 50 (for example one or more processors or display devices) are remote from the other parts of system 10 and connected by wired or wireless communications for example nearby but in another room of a hospital department, or in other cases more remote and in communication over the Internet. If all portions of system 10 are in one place and connected, system 10 can also be referred to as an apparatus 10 or device 10.

Pressure to the IJV applied in accordance with the present invention in some patients initially causes an elevation of the amplitude of brain pulsation. Additional applied pressure results, in these patients, in a decrease of amplitude to a more compressed line. Pressure to IJV causes a decrease of pulsation variability in the brain until it becomes a relative straight-line. The amount of time until this happens correlates with the magnitude of the original ICRS capacity.

While amplitude of the ICP waveform has been discussed, this is not the only measure of ICP waveform variability useful for the present invention. In one embodiment, variability of the intracranial brain tissue pulsation waveform comprises at least one of the following ICP waveform parameters: (i) a variability of an amplitude of the waveform and (ii) a variability of an area under the curve of the waveform, (iii) a variability of a dominant frequency of the waveform (for example a frequency between 0.1 and 35 MHz), (iv) a direction of high frequency shift (for example of between 12 and 35 MHz) of the waveform (which affects the amplitude and hence variability of the waveform), (v) a phase shift of the waveform (which affects the amplitude, and hence variability, of the waveform and (vi) a variability of a multiaxial spectroscopy of the waveform (ICPWMS). In another embodiment, variability of the intracranial brain tissue pulsation waveform comprises a variability of at least one of the following ICP waveform parameters: (i) an amplitude of the waveform, (ii) an area under the curve of the waveform, (iii) a dominant frequency of the waveform (for example a frequency between 0.1 and 35 MHz) and (iv) a multiaxial spectroscopy of the waveform (ICPWMS). The spectroscopy referred to herein is a mechanical motion (pulsatility) spectroscopy, not a magnetic or electrical spectroscopy. Other functions that quantify variability of the ICP waveform are also within the present invention, including but not necessarily limited to combinations and/or derivatives of the above six examples of ICP waveform variability indicia/parameters.

In order to determine if the amplitude or other characteristic of the intracranial brain tissue pulsation waveform has reached a predefined decline in variability, for example as shown in FIG. 9, according to one embodiment, a comparison of variability during a predefined period of time is made with a previous variability during a preceding period of time and this is performed by one or more processors of the computer system 50, in accordance with special purpose software. Variability is defined, according to one option, by the difference between the highest and lowest amplitude (or other waveform variability characteristic) during a certain period or cycle. For example, the predefined decline in ICP waveform variability is defined such that variability of an amplitude (or of other waveform parameter indicative of variability) of the waveform during the predefined period of time is ten percent (or in other embodiments 5%, 15%, 20%, 30%, 40%, 50%, 60%, 70%, 80% or 90%) or is no more than ten percent (or in other embodiments no more than 5%, 15%, 20%, 30%, 40%, 50%, 60%, 70%, 80% or 90%) of a variability during a previous period of time of predetermined length. In other words, the waveform has compressed to such an extent that its variability is only 10% of what it previously was, for example during a previous cycle. In one example, the predefined decline in variability of the waveform is defined such that the waveform has compressed 80% such that its variability has become only 20% of what it was previously.

In some embodiments the "previously" that it is compared to is the variability of the waveform during a previous cycle, or in other embodiments during an average of certain previous cycles such as an average of the variability during the preceding 2 cycles, or during the preceding 3 cycles, or during the preceding X cycles, wherein X can be any positive integer.

In another example, the predefined decline in variability is defined such that once the decline in variability has persisted for at least a certain amount of time or at least a certain number of predefined periods of time or cycles, only then is it counted as having achieved the required decline in variability. Since the predefined decline in variability is quantified, according to one embodiment, the computer system signals that the interval end time has been reached, thereby triggering the computer system to calculate the time interval, which represents how long it took for the ICRS to become "occupied".

Figure 8:
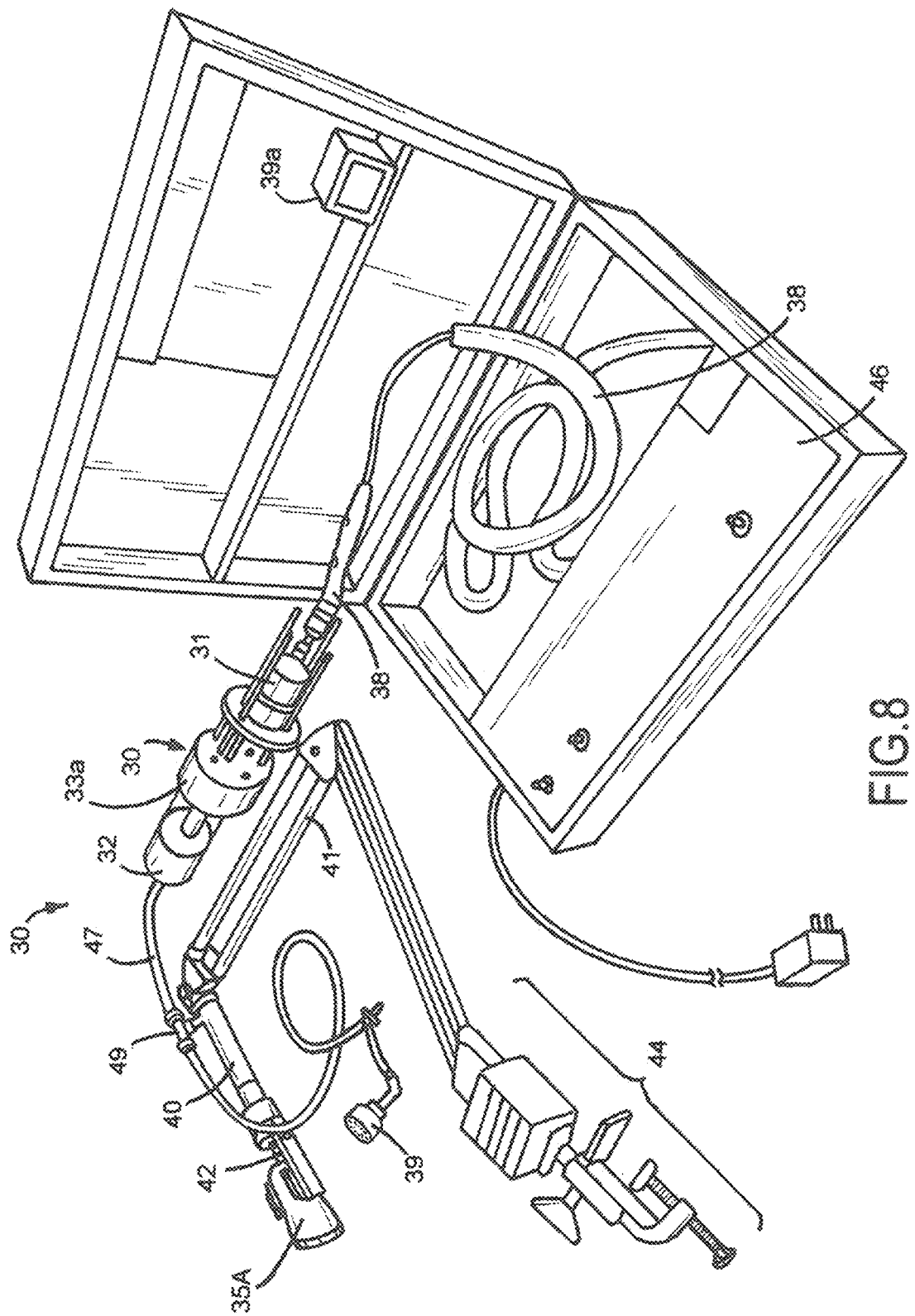
FIG. 8 is a perspective view of a pressure-application and pressure-measuring instrument and holder guided by a 2-dimensional ultrasound image and applicable to a cavity, vessel and tissue of a subject, in accordance with one embodiment of the present invention.

The pressure application instrument 30, in some embodiments, is configured to also measure the pressure at the internal jugular vein (IJV) using a manometer 39, as shown in FIGS. 3, FIG. 6 and FIG. 8. Instrument 30 is configured in certain embodiments to apply an initial pressure and subsequent greater pressures in uniform stepwise increments to the internal jugular vein. For example, in one particular non-limiting embodiment, an initial pressure of 1 mm Hg is first applied non-invasively at the subject's skin at the IJV (at the neck), then a pressure of 2 mm Hg is applied, then 3 mm Hg, then 4 mm Hg, then 5 mm Hg, and this stepwise upward progression is continued until the predefined decline in variability of the intracranial brain tissue pulsation waveform is detected from the display visually by the human user, or more preferably automatically by the computer system when the special purpose software treasures the variability of the waveform dynamically. The detection of the compression in the waveform to a predefined decline in variability is one or a combination of ti) a visual detection by the user and more preferably (ii) a predefined alert by the computer system according to quantitative criteria written into the software 55, for example special purpose software 55. The alert may be based on at least one of (i) the length of time (T) and (ii) an intracranial reserve space capacity. It may also be based on the amount of pressure applied by instrument 30.

Figure 6A:
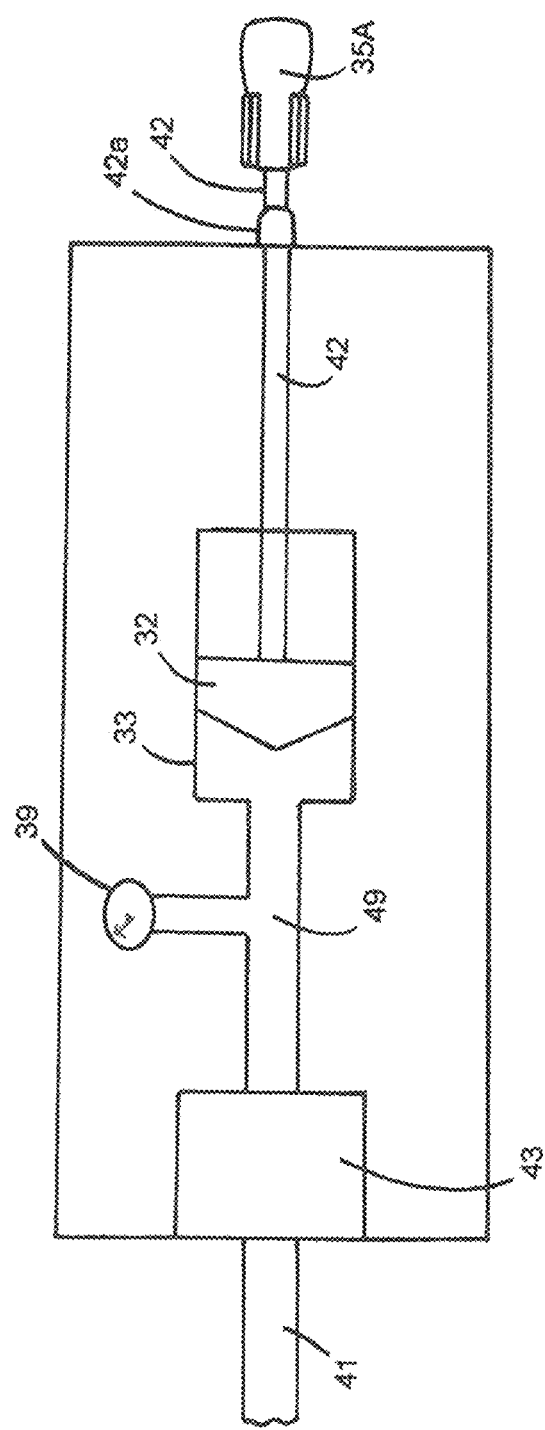
FIG. 6A is a schematic view of a pressure application and measuring instrument, in accordance with one embodiment of the present invention.
Figure 7:
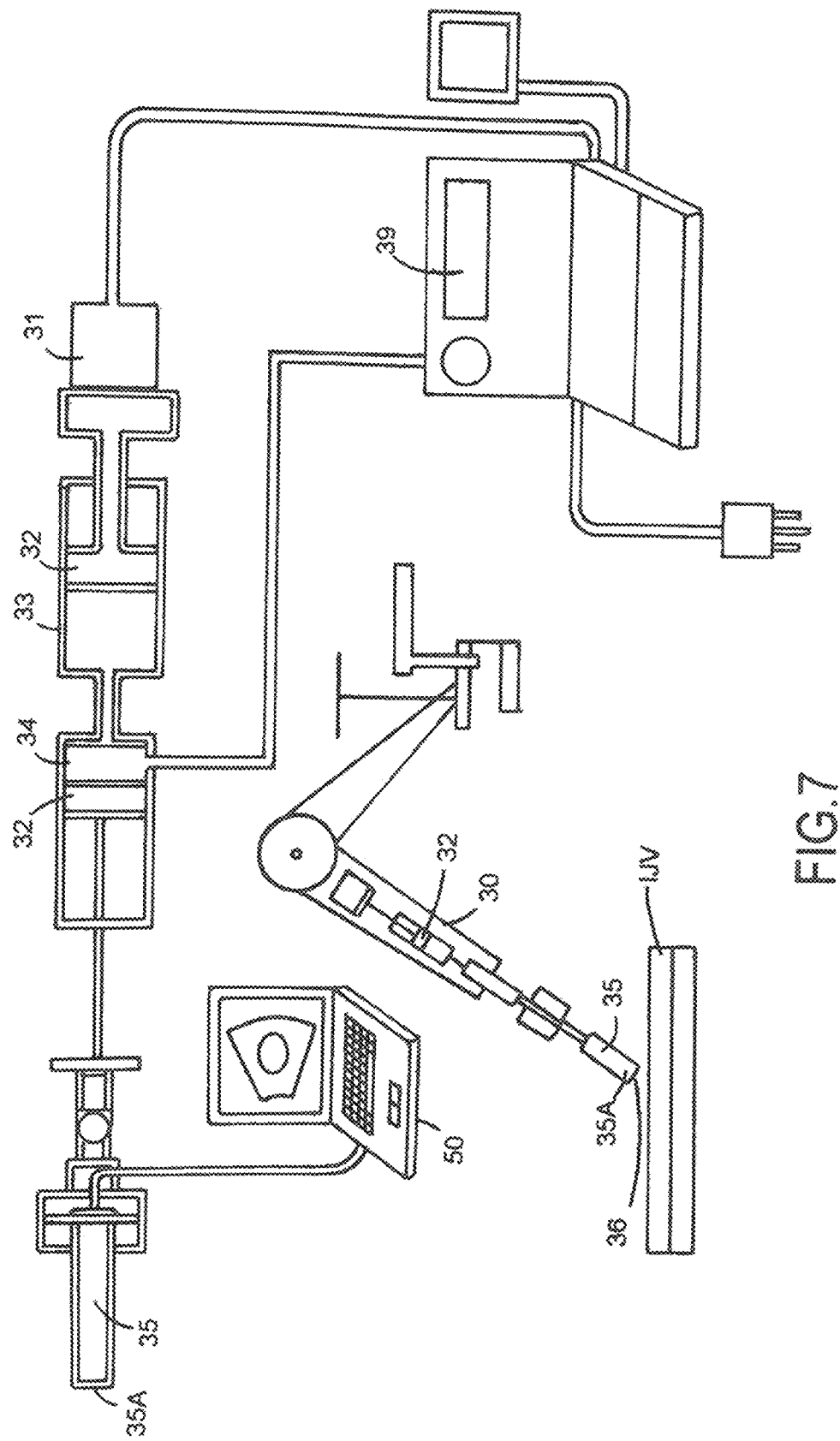
FIG. 7 is a schematic view of a pressure application instrument, holder, laptop and display and battery charging device and digital manometer, in accordance with one embodiment of the present invention.

The instrument 30 is shown in FIGS. 6-8. Instrument 30, as shown in FIG. 8, is a pressure applying and pressure sensing device guided by a 2-dimensional ultrasound image for highly accurate pressure measurement on a cavity, vessels and tissue of a subject. As shown in FIG. 6 and FIG. 8, in certain embodiments one way of implementing this is that the incremental increases in pressure driven by a motor 31 and piston 32 causes air or another fluid to travel through tube 47 and to a triple angle connector 49. In some embodiments there are multiple pistons, as is known in the art of controlled fluid dispensers such as syringes. Some of the fluid then travels past the triple connector 49 to manometer 39 while other portions of the air or another fluid enters pipe 40. In some embodiments, the incremental increase in pressure in pipe 40 causes pipe 40 to pivot at pivot point P (FIG. 6) and flex on its axis with holder 41. Holder 41 is in some embodiments fixed to a static structure by a fixing component 44 (FIG. 8). This pivoting or rotation of pipe 40 also generates a forward linear motion by probe 35A against the neck or other body part of the subject incrementally.

In some embodiments, pipe 40 has an inverted piston 42 movable within it. Inverted piston 42 may be attached on its distal end, as shown in FIG. 6 and FIG. 8, to probe 35A. Although FIG. 6 depicts the connection between probe 35A and inverted piston 42 as linear, in certain embodiments, the connection between probe inverted piston 42 and probe 35A in certain embodiments permits a change of angle between probe 35A and inverted piston 42. For example, in one embodiment, along the connection between probe 35A and inverted piston 42 is a joint 42A that permits multiple degrees of freedom, including in one embodiment six degrees of freedom, for probe 35A, something that facilitates manipulation of probe 35A through forty-five degree or other angles in accordance with Doppierography. In FIG. 8, for example probe 35A is angled relative to inverted piston 42.

The instrument 30 in some embodiments shown in FIG. 7 includes a motor 31, at least one piston 32 movable within a housing 33 such as a syringe 33 (having syringe cover 33A), a source of liquid or gas fluid 34, for example air, and an applicator 35 whose distal end 36 is shaped to engage the neck of the subject. The applicator 35 includes an ultrasound probe 35A (not to be confused with probe 20 used at the head of the subject) whose signal is converted to an image of the IJV. Ultrasound probe 35A includes in some embodiments a Doppler ultrasound output for measuring the linear velocity of the blood flow at the IJV. This makes it possible to obtain the ICRS parameter of ICRS capacity which depends on linear velocity of the IJV. Without this Doppler ultrasound output it is possible to obtain the ICRS parameter of length of time (T) for ICRS to be occupied although not the ICRS parameter of the ICRS capacity. As seen from FIG. 8, motor 31 is connected to a power supply 38 and a charger in some embodiments. FIG. 8 also shows digital manometer 39A to show a digital version of the pressure and computer 46 along with battery charger. The computer interacts with compressor 43 (FIG. 6A) or motor 31 (FIG. 6, FIG. 7) to determine what volume of fluid, such as air, to send to the pipe 40.

FIG. 6A shows a different embodiment of instrument 30 in which an impulse compressor 43 produces uniform amounts of air that can be incrementally adjusted as in FIG. 6.

The multi-dimensional probe 20 is a modified version of a standard USB compatible ultrasound probe, such as a modified version of the standard USB compatible probes manufactured by Interson corporation of California. Probe 20 preferably should be modified in several ways, in accordance with some embodiments. First, as shown in FIG. 1C probe 20 has in some embodiments a mechanism for dispensing a gel. For example, probe 20 in some embodiments has an automatic gel dispenser 26 which may include a gel reservoir 28, a tube 26b for gel transfer, a micromotor/microengine 29 and an actuating mechanism such as a button 26a. Second, as shown in FIG. 1C, the distal end of the probe 20 is configured to grip the skull 11. For example, in some embodiments the distal end of probe 20 is concave and has a shape that is adjustable so as to conform to an outer surface of the skull 11 of the subject. In some embodiments, for example, one or more springs 27 (FIG. 1C) are situated behind and connected to each piezoelectric crystal 22—or group of crystals—of the crystal array 22 of the probe 20. Third, the probe 20 is a multi-frequency probe whose emitter and receiver have different frequencies. In one example, the emitter has a frequency of 0.5 to 2 MHz and the receiver has a frequency of 1 to 4 MHz which may be double the frequency of the emitter frequency in some embodiments.

Figure 3B:
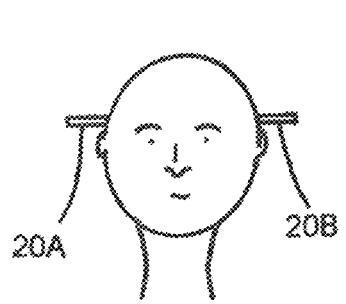
FIG. 3B is a schematic view of one mode of application of probe 20 to a subject's head where the receiver 20B is on the opposite of the head from the emitter 20A.
Figure 3C:
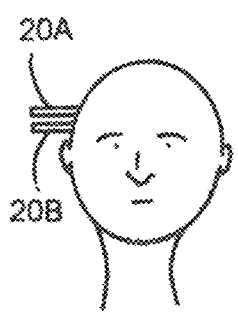
FIG. 3C is a schematic view of a second mode of application of probe 20 to a subject's head where receiver 20B is adjacent emitter 20A on the same side of the head.
Figure 4:
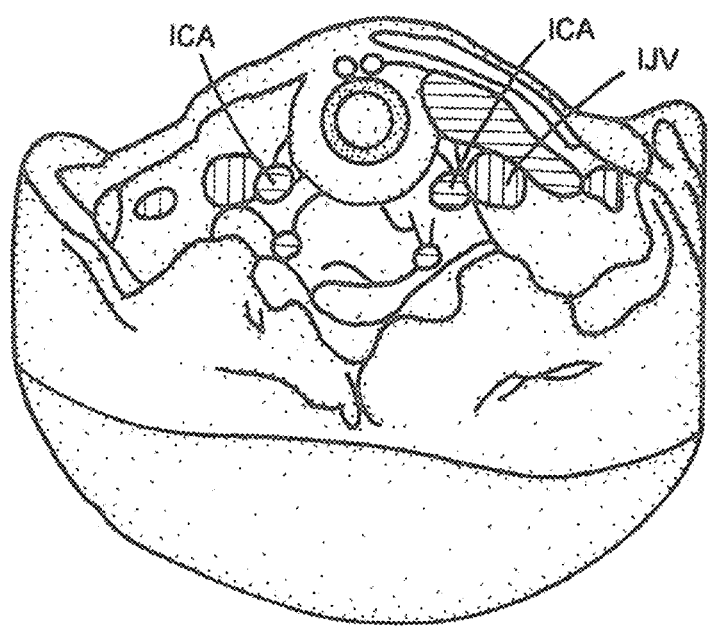
FIG. 4 is an anatomy of a cervical axial slice of a subject showing an internal jugular vein (ITV) and cervical portion of the internal carotid artery (ICA)
Figure 5:
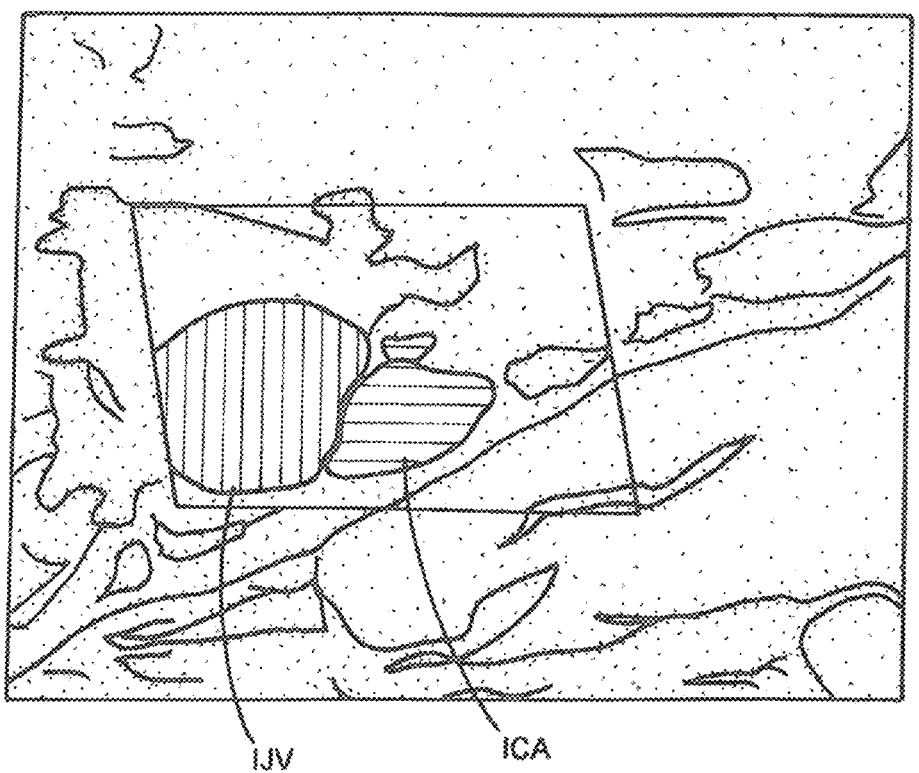
FIG. 5 is a Doppler ultrasound image of the internal jugular vein and adjacent internal carotid artery of a subject, used in accordance with one embodiment of the present invention.

In addition, in some embodiments shown in FIG. 3B the probe 20 has only a transmission mode having continuous voltage in which the emitter 20A of probe 20 is on one side of the head and the receiver 20B of probe 20 is on the opposite side of the head of the subject. In a different embodiment shown in FIG. 3C, probe 20 has both a continuous transmission mode (called "transmission mode") and a discrete transmission mode (called "impulse mode") which can be referred to as integrative mode in which the emitter and receiver of probe 20 are adjacent and preferably integrated into one device and applied to one side of the head. The impulse mode involves discrete non-continuous application of voltage. For example, as shown in FIG. 1B, a central section of the probe 20 having the central piezocrystal array 22 emits in transmission mode and the side (lateral) sections of the probe 20 having the side piezocrystal mays 22A receiver at a different frequency and in impulse mode. This is also integrated into one device. The integrate mode is better because the signal to noise ratio is ratio is much higher and signals emitted are amplified. Since the different parts of the head are non-homogeneous and have different acoustic impedance, the border points between the materials of different impedance generate reflecting waves in different directions toward the receiver of the probe 20.

The two-dimensional USB port compatible probe 35A of instrument 30 used for imaging the internal jugular vein to see (for example to see when it is partially occluded) is an ultrasound probe that in some embodiments has a frequency such as 6-7.5 MHz, or generally between 3.5 MHz and 24 MHz. For example, the ultrasound probe 35A transmits the signal to the computer system and the computer system presents to the user a dynamic image of the internal jugular vein. The image preferably is of a cross-section of the IJV. The cross-sectional area of the IJV, or in other embodiments the diameter of the IJV, is determined either automatically by the computer system 50 or estimated by the user visually from the image produced by the display.

Both probe 20 and single frequency probe 35A may be structured such that the electronics, which is heavy, is distanced by a connecting cable from the piezoelectric array of crystals to provide greater flexibility in use of each of the probes 20, 35A. The cable is grounded to block influence from an EMF field. Preferably, both the two-dimensional probe 20 and the singe frequency probe 35A are mechanical scanning probes that move the emitters and receivers. The sector of the image generated by the probe 20 is shown in FIG. 3A. In another embodiment shown in FIG. 1B, static arrays of emitters and receivers having a shape that provides the sector is depicted. FIG. 1B shows both a central piezocrystal array 22A and lateral piezocrystal arrays 24. The lateral piezocrystal arrays are also called side piezocrystal arrays. There is, in certain embodiments, as shown by FIG. 1B an angle between the central piezocrystal array 22A and the lateral piezocrystal arrays 24. This angle is 10 degrees on one side and 15-20 degrees on the second side, in some embodiments. This difference in angles provides greater versatility for probe 20 since skulls vary amongst humans.

As shown in FIG. 1CA, as an alternative embodiment to that shown in FIG. 1C, springs 27 are situated on each horizontal end in order to maintain the piezoelectric crystals 22 that are at the ends of the crystals 22 facing the skull 11 of the subject (as opposed to the ends facing the springs 27). Since the skull 11 may vary from one person to another, each group of piezoelectric crystals other than the central group has a separate spring 27 adapted to cause the array of crystals to engage the skull 11.

As seen from FIG. 7, the instrument 30 is connected to a manometer 39. This provides the IJV pressure for calculating the ICRS per pressure. In some embodiments, the ICP is also measured and the combination of parameters is used to determine medical decisions. For example, if the ICP is known to be low enough then it is recommended to measure and monitor ICRS.

Figure 1B:
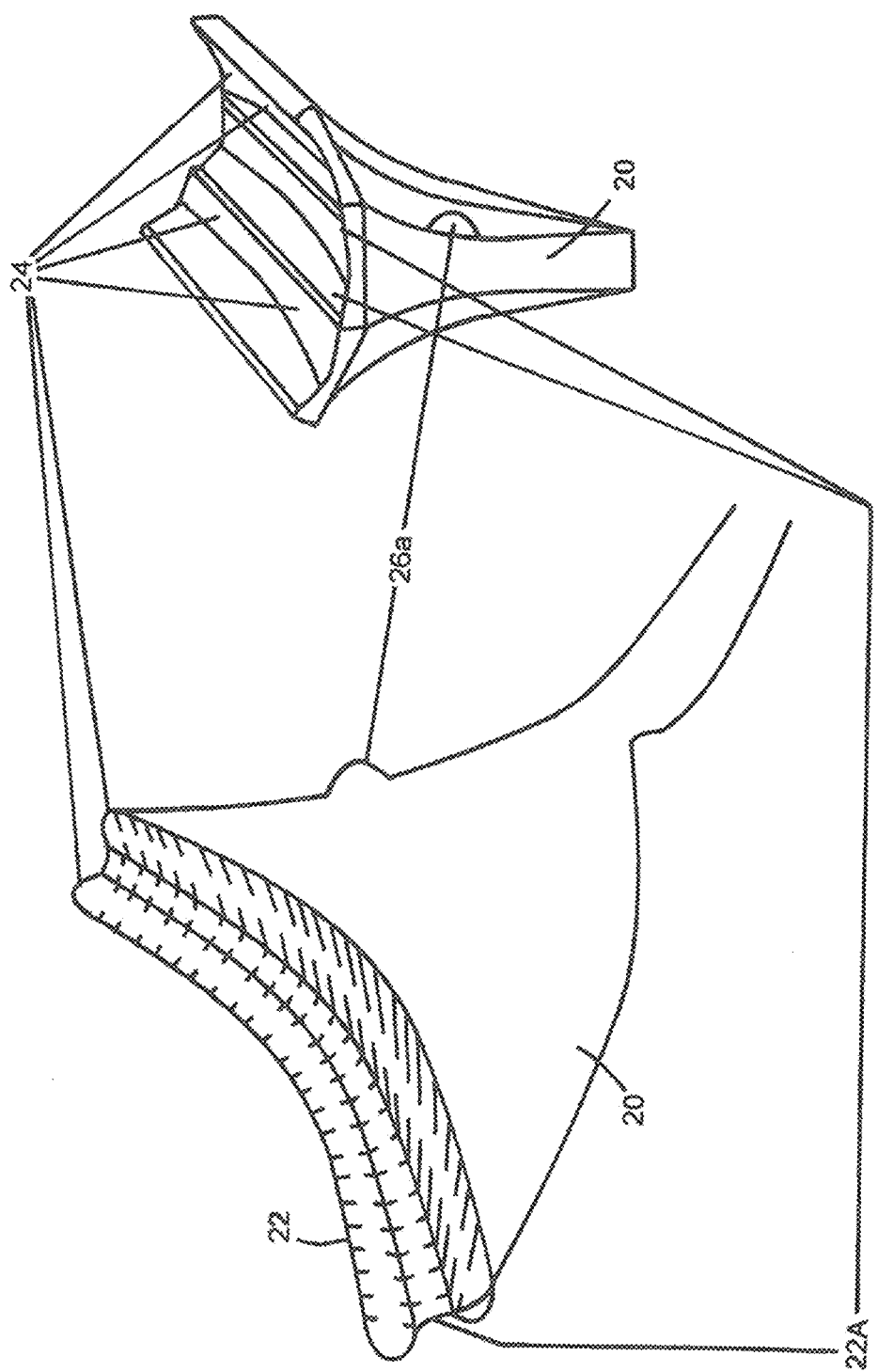
FIG. 1B is a perspective view of the ultrasound probe of FIG. 1A, in accordance with one embodiment of the present invention.
Figure 1C:
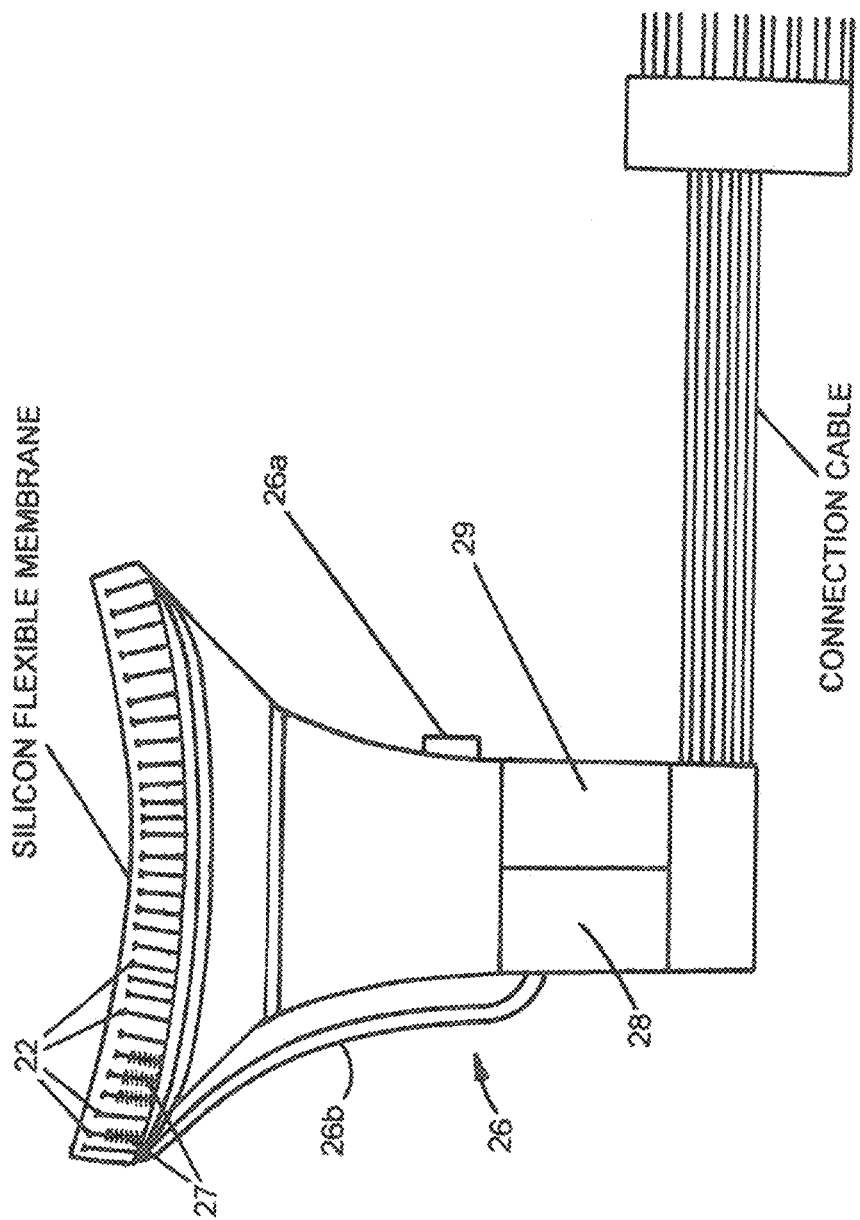
FIG. 1C is a lateral side view of the ultrasound probe of FIG. 1A, in accordance with one embodiment of the present invention.
Figure 1C:
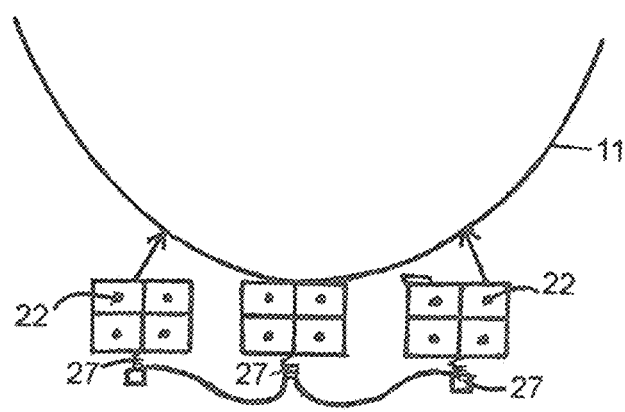

Referring now to FIGS. 1A through 1C, there are shown, by way of example, a novel ultrasound probe 20 used for intracranial space measurement in accordance with one or more embodiments of the present invention. In the embodiments shown in FIGS. 1A-1C, ultrasound probe 20 is designed to be adjustable to suit the curvature of the skull 11 surface, which varies from one individual to another. Thus optimal contact is assured, for best definition. The probe 20 has ultrasound multi frequencies and multi-axial mode. The probe is able to scan towards any spatial angle or dimensional axis (as compared to prior art single-dimensional probes). Additionally shown in FIG. 1C, the ultrasound probe 20 may include a gel reservoir 28, for example an acoustic gel reservoir, which may be mechanically activated to release and apply ultrasound gel upon the skull.

The central part of the probe, shown in FIG. 1B, includes 2D piezocrystals 22 with ultrasound carrier frequency of 0.8 MHz, and on the two sides of probe (receivers) with receiver frequency ranges from 1 MHz to 2 MHz, more preferably between 2 MHz and 4 MHz. By selecting successive subset of probes from the array, successive contiguous groups of probes and successive focal points, a series of pixels within the tissue may be observed which cover the entire volume of the tissue at a resolution dependent on the pixel size. In some embodiments, the probe is moved to various locations upon the skull, and optionally these sector scans are combined using relevant software, to obtain a scan inclusive of all anatomical regions of import. Certain embodiments of the present invention are thus equivalent to ultrasound computer tomography, without its disadvantages, such as that the claimed invention can be implemented dynamically and without harmful radiation.

As shown in FIG. B, ultrasound probe 20 in some embodiments is configured in a shape to be held adjacent a skull of the subject for example at the top of the head. In some embodiments, an adjustable flexible rectangular array 22 of ultrasound piezoelectric crystal array 22, for example including lateral piezoelectric arrays 24 and a central piezocrystal array 22A, as shown in FIG. 1B, is arranged in a custom-made array in which is brought in contact with the skull. An adjustable flexible rectangle array of ultrasound probes is arranged in a custom-made array 22 which is brought in contact with the surface of the skull more effectively.

In prior art ultrasound probes, the emitter and receiver typically operate within the same frequencies, and thus are unable to penetrate the skull at the typical frequencies (3-10 MHZ) used to view other human tissues. In contrast, in accordance with one particular embodiment of the present invention, the emitter of probe 20 may emit at 0.5-3 MHZ while the receiver of probe 20 receives at approximately 1.0 MHz-6 MHz, which provides a high resolution scan. In accordance with one embodiment, the probe 20 of the present invention uses a low frequency (0.5 MHz to 3.0 MHz, for example 0.8-2.6 MHZ, for example 1.7 MHz) ultrasound emitted signal as there is little attenuation of the skull at these frequencies. However, the receivers of probe 20 are high frequency receivers in the range of 1 MHz to 6 MHz, more preferably between 1 to 4 MHz (which provides high resolution). In general the emitting frequency is lower than the receiving frequency and in one embodiment both emitting and receiving frequencies are between 0.5 and 3.5 MHz. Typically, the receiving frequency is roughly twice the emitting frequency. In one particular embodiment, the ultrasound probe 20 emits at a frequency of about 0.5 MHz and receives at a frequency of 1.0 MHz. In one other particular embodiment, it emits at 1.76 and receives at 3.5 MHz. In one other particular embodiment, the ultrasound probe 20 emits at a frequency of about 1.0 MHz and receives at a frequency of up to about 1.7 to 1.8 MHz, and in one embodiment 1.76 MHz, using a carrier emitter frequency of about 0.5 MHz to 1.8 MHz, and in particular an emitter frequency of 0.5 to 1.76 MHz.

As a result of the dual range frequency ultrasound probes, ultrasound power is less attenuated by bones through which the ultrasound waves travel. In addition, the visual spatial resolution of the brain tissue image is good. For example, in some embodiments the resolution of the ICP waveform (or waveform pattern) is more than 3000 points per cycle, for example more than 4000 points per cycle or more than 5000 points per cycle or more than 6000 points per cycle. This provides an advantage over the resolution achieved by the prior art, which is 3000 points per cycle. Reflected ultrasound energy from the tissue is received via the probes and then converted into output signals. A high resolution, fast processing unit will process these output signals from the probes, and determine the pulsatile activity and characterize the response status of the tissue target. This information is then transformed into quantitative measurements of tissue characteristics and intra tissue pressure.

As shown in FIG. 2A (see "point I and "point II"), in some embodiments, multi-frequency ultrasound probe 20 is configured in some embodiments to receive ultrasound waves from at least two different intracranial locations. As shown in FIG. 2A, in some embodiment the two different intracranial locations are dissimilar according to predetermined criteria. The computer system 50 is configured in some embodiments to determine a representative ICRS parameter from separate respective ICRS magnitudes at the at least two different intracranial locations. In one embodiment, these two different locations are preferably unlike one another, for example one location could be a surface of the cranium and a second location could be the third ventricle (or tissue that is located between the surface of the cranium and the third ventricle). In one embodiment, when the user applies probe 20 to a first of the different locations, the user situates the probe 20 horizontally whereas when the user applies probe 20 to a second of the different locations, the user situates the probe 20 vertically. In another embodiment, when the user applies probe 20 to a first of the different locations, the user situates the probe 20 vertically whereas when the user applies probe 20 to a second of the different locations, the user situates the probe 20 horizontally. In either of these two embodiments, applying the probe 20 in both horizontal and vertical positions enhances the accuracy of the data obtained for the ICP waveform.

In some embodiments, computer system 50 is further configured to convert the signal received from probe 20 into a dynamic image of a pulsatility of brain tissue, and in particular a multiaxial pulsatility or a three-dimensional pulsatility of brain tissue, in at least a part of the head that the probe received ultrasound waves from. System 10 includes all hardware and software necessary to implement this, including in some embodiments, special purpose software configured to convert the signal into multi-dimensional brain tissue pulsations and to derive real time digital intracranial pressure waves. The multi-dimensional pulsations in some embodiments include all three mutually perpendicular planes for multiaxial directions including in some embodiments multiple oblique directions in each of the three mutually perpendicular planes. The dynamic image of brain tissue pulsatility is displayed on a computer display for the user to see. The image of brain tissue pulsatility is a continuous dynamic image in some embodiments. Some embodiments of the present invention provide the possibility of fourfold magnification of the images of the brain pulsation, which makes it much easier to see very tiny pulsations of brain tissue. In some embodiments, this provides visualization in real time of the brain tissue moving in three dimensions, by means of special purpose software. This provides a visual display of the brain tissue to the physician, technician or user. However, even without this, the present invention is able to determine the length of time (T) from partial occlusion of the IJV until the variability of the ICP waveform has been compressed and from this to calculate the ICRS capacity and whether the ICRS is normal, too large or too small.

As a result of the computer system 50 monitoring one or more intracranial reserve space parameters, and in some embodiments also the intracranial pressure, the computer system 50 is configured to send an alert that the ICRS is abnormal such that an action, such as a surgery is needed or such that clinical deterioration of the subject is either predicted to occur or inferred to have occurred based on an abnormal ICRS.

In certain embodiments, the computer system is further configured to determine a magnitude of an intracranial reserve space (ICRS) parameter. One such parameter is the length of time from the partial occlusion until the amplitude or other waveform parameter achieves a predefined level of variability decline, for example flattening out to a predefined percent of previous variability. This length of time parameter provides information as to whether the ICRS is normal, too large or too small, by inference. This determination of whether the ICRS is too small, normal or too large may consider the age of the subject and other suitable characteristics. In some embodiments, this determination considers the ICP of the subject, for example an ICP of the subject as determined by an embodiment of the present invention.

In some embodiments, the computer system 50 is configured to determine the magnitude of an ICRS parameter from a volume velocity (V) of venous blood output occluded at the internal jugular vein (in some embodiments also taking into consideration the ICP or pressure at the IJV) taking into consideration the length of tune (T) of application of the pressure. In this case the ICRS parameter is the capacity, in volume, that the ICRS can hold from the extra volume of intracranial blood that is blocked from exiting the cranium after partial occlusion of the IJV until the variability (for example amplitude) of brain tissue pulsations declines by a predefined level. This is called "ICRS capacity". It is noted that the blocked venous blood pushes the CSF to exit the cranium into the spinal canal. Only a small portion, approximately 5-10 cc out of 70-80 cc, of the CSF exits into the spinal canal before the ICRS can be considered "occupied" and the amplitude or other variability indicator of the ICP waves flatten (due to the space limitations of the spinal canal). Accordingly, the "ICRS capacity" as used herein is not the actual true volume of the total ICRS but is rather merely the available capacity of the ICRS (for example to hold extra venous blood) before the variability parameter such as amplitude of the ICP waves flatten (as defined quantitatively) and the ICRS is deemed "occupied". The ICRS is deemed "occupied" when the ICP wave amplitude (or other selected variability parameter of the ICP waves) compress to the point of being flattened (as defined by the user preferably quantitatively, or in other embodiments visually).

For example, the computer system 50 in some cases makes use of a mathematical relationship V·T·C=ICRS volume, which equals the volume of extra intracranial blood that "occupied" the ICRS due to the partial occlusion of the IJV, wherein V is the volume velocity of venous blood blocked (volume velocity being linear velocity times cross-section) over T seconds times C, which is the proportion of the IJV that has been occluded by the partial occlusion, and which in some embodiments is the percentage of the cross-section of the IJV that was occluded by the partial occlusion, for example 0.05 (i.e. 5% occlusion) or 0.10 (i.e. 10% occlusion) 0.15 (i.e. (15% occlusion) or another percentage between 5% and 25% or in some examples between 5% and 15% of the initial (pre-occlusion) cross-section of the IJV. Note that the percentage of the cross-section is a scalar value rather than a variable. The partial occlusion may also be measured by a percentage of the initial (pre-occlusion) diameter (or in some embodiments the radius) of the IJV occluded, for example 2.5% or 2.5% to 8% of the diameter of the IJV or from 2.5% to 13% or from 2.5% to another percentage between 2.5% and 13%. Generally, use of the cross-section is more precise than use of the diameter.

The exact percentage of the partial occlusion of the IJV implemented may depend on the individual. A child or a person with high ICP may be given a partial occlusion of 5%. An elderly person or a healthy patient with normal ICP may be given a partial occlusion of 20%. These are non-limiting examples.

Equation (1): ICRS=V·T·C, wherein V is the volume velocity (linear velocity times cross-sectional area of the IJV) of the blood flowing across the IJV for example just before partial occlusion, wherein T is the length of time from partial occlusion until a predetermined decline in variability of the ICP waveform occurred and wherein "C" is the percentage of the cross-section of the internal jugular vein that has been partially occluded. The cross-section of the IJV and the linear velocity of the blood through the IJV is determined by the computer system using a signal of the ultrasound probe 35A of instrument 30 having a Doppler measurement feature.

The units obtained are distance cubed, such as centimeters cubed. The units of centimeters cubed are derived by multiplying cm/sec (the units for linear velocity) by $(cm)^2$ (the units for cross-section) and by seconds (the units for time). Stated mathematically, the units derive from: $(cm/sec)\cdot(cm)^2\cdot sec=(cm)^3$ The "ICRS capacity" corresponds to the available volume of intracranial reserve space that existed before the partial occlusion of the IJV caused the extra blood within the cranium to occupy the intracranial reserve space—by pushing the CSF out of the cranium into the spinal canal—until the brain tissue pulsations were compressed. This volume parameter, as well as the length of time it takes for the ICRS to be "occupied", are useful to neurosurgeons and others in making determinations as to the tentative diagnosis of the patient, what treatment to administer and the prognosis. In accordance with the certain embodiments of the system and method of the present invention, this parameter is non-invasively measured repeatedly, for example multiple times within a period of time of an hour or multiple times within X minutes, wherein X is 15, 30, 45, 60, 75, 90, 120, 150, 180, 200, 250, 300, 350, 400 or 500 or multiple times within X hours, wherein X is 0.1, 0.2, 0.3 . . . 0.9 or 1.0, 2, 3, 4, 5, 6, 7 8, 9, 10, 11, 12, 18, 24, 36, or 48 or a greater number of hours, or daily or weekly or bi-weekly or monthly or bi-monthly or quarterly or semi-annually or annually or at greater intervals. The repeated measurements are at uniform intervals in some embodiments. In other embodiments, the repeated measurements are not at uniform intervals. The ICRS parameter (for example either length of time T or ICRS capacity) is measured dynamically in some embodiments. Each time the ICRS parameter is measured, the instrument 30 is applied to the internal jugular vein of the patient again. However, the length of time that this pressure is applied is too small for it to be a danger to the patient. For example, one embodiment, the is partially occluded for 3 to 5 seconds.

It is not dangerous to partially occlude the internal jugular vein on one side of the neck. The Quickenstedt maneuver, although now considered unnecessary due to better imaging modalities like MRI and CAT, was used by the medical profession for many decades to diagnose spinal stenosis. This maneuver involves fully occluding both internal jugular veins for 10-12 seconds. See https://en.wikipedia.org/wiki/Queckenstedt's_maneuver.

In certain embodiments, after repeating the determination of the ICRS parameter one or more times, for example length of time (T) or ICRS capacity, in certain embodiments, the computer system 50 makes a prediction as to whether clinical deterioration of the patient will occur. In certain embodiments, after repeating the determination of the ICRS parameter, for example length of time (T) or ICRS capacity, in certain embodiments, the computer system 50 makes a prediction as to whether the patient will experience elevated ICP. In each case (prediction of clinical deterioration and/or prediction of elevated ICP) the prediction may include a level of certainty and/or a time by which the prediction is expected to occur. The level of certainty may be expressed in terms of probability or any other suitable format known in the art. Further, in some cases, the prediction only occurs after multiple instances of the determination of the ICRS parameter being repeated, or only after a predefined length of time elapses during which the potential prediction is repeated, wherein a "potential prediction" refers to an output of a prediction by computer system 50 that is not formalized into art official diagnostic prediction until a predefined length of time elapses during which the potential prediction is repeated.

Accordingly, in some embodiments, the computer system 50 is configured to predict for the mammalian subject, for example a human patient, at least one of (i) an elevated ICP of the subject and (ii) clinical deterioration of the subject, the prediction being derived from the ICRS parameter, wherein the ICRS parameter is at least one of (i) the length of time (T) and (ii) the intracranial reserve space (ICRS) capacity.

V is the volume velocity, V, (linear velocity times cross-section of IJV) of the blood outflow blocked at the IJV divided by the pressure, P, in mm Hg applied at the IJV, and T is the time from the partial occlusion until the ICP waveform is compressed at a predefined amount, such as when the amplitude of the ICT waveform declines a predefined amount such as 90%. C is the percentage of the cross-section of the IJV that was occluded. The units of the ICRS parameter are therefore $cm^3$ (or other distance units cubed) per mm Hg (i.e. volume per pressure). This provides a measure of the blood outflow blocked and caused to accumulate in the cranium for a given pressure in mm Hg applied to the IJV during a given length of time.

In some embodiments, and because what constitutes a normal ICRS varies with the ICP of the individual, the computer system 50 is configured to determine the ICRS/ICP Pressure rather than the ICRS capacity. The ICP may be supplied from another source such as a direct invasive source or it may be supplied by the non-invasive system of the present invention. Accordingly, the computer system according to this embodiment is configured in some embodiments to determine ICRS/ICP from the volume velocity of the IJV (linear velocity times cross-section of vein) times T (duration of time during which partial occlusion occurred) and times C, the percentage of the cross-section of the IJV that was occluded by the partial occlusion, for example 0.05 (i.e. 5% occlusion) or 0.10 (i.e. 10% occlusion) 0.15 (15% occlusion) or another percentage between 5% and 15% and divided by pressure (P)=to yield ICRS absolute volume per units of pressure or cm cubed per mmHg. The pressure (P) used for this equation is the pressure IJV at a time when the IJV pressure is deemed to correspond to or be equal to or approximately equal to the ICP pressure, namely (assuming the ICP is not otherwise available from an invasive source or from another source and is supplied by the present invention) when a variability characteristics of the ICP waveform begins to decrease in variability as measured by amplitude or another variability characteristic.

The reason that IJV pressure is assumed to equal ICP at that point is that, after partial occlusion, once brain tissue pulsations start to decline as evidenced by amplitude or another ICP waveform characteristic that declines, there is a shortage of space in the areas of the cranium where the brain tissue pulsates. This means that the partial occlusion at the IJV has been strong enough to overcome the flow of venous blood from the cranium to the IJV, and the upstream effects in the cranium reflect this. This means blood is not flowing between the cranium and the IJV which indicates equal pressure at both the IJV and the blood in the cranium. Applicant is measuring ICP by a method analogous to arterial blood pressure on the arm. In this case, the force of the partial occlusion is sufficient to decrease ICP wave amplitude (or other variability parameter) in the brain.

Equation (2): $ICRS=V/P\cdot T\cdot C$, wherein V is the volume velocity of the blood flowing across the IJV for example just after partial occlusion, wherein P is the pressure at IJJ at a time when such pressure corresponds to ICP, namely when decline in variability of ICP waveform commences, wherein T is the length of time from partial occlusion until a predetermined decline in variability of the ICP waveform occurred and wherein "C" is the percentage of the cross-section of the internal jugular vein that has been partially occluded.

P as used in the above equation (2) can also be thought of as the pressure to IJV necessary for decreasing of venous output and decreasing of ICP waves variability (for example amplitude) to a predefined degree of compressed state. Likewise, T as used in equation (2) can be thought of as the time needed for pressure, P, to IJV to generate this decrease of ICP wave variability (i.e. brain pulsation effacement). The linear velocity and cross-section of the IJV or ICA is obtained by the computer system directly from the ultrasound probe 35A which is at the distal end of the pressure application instrument 30 applied to the subject's neck on the supine position on the level C3 C4 vertebrae. This probe 35A should not be confused with the ultrasound probe 20 place on the patient's skull. In some embodiments, one or more processors of the computer system are configured to determine an ICRS parameter from a relationship of $\Delta V/\Delta P$, wherein $\Delta V$ is the difference in volume velocity between two points in time and wherein $\Delta P$ is the difference in pressure between two points in time.

Accordingly, the computer system 50 of system 10 is configured in some embodiments to send an alert or to display a determination of an ICRS parameter, for example an absolute volume comprising or corresponding to the ICRS capacity, or a volume divided by a pressure corresponding to the ICRS per unit pressure. The pressure is the IJV pressure at a time when it is understood to equal or approximately equal the ICP pressure, for example at the beginning of decline in variability of the ICP waveform. This determination of the ICRS parameter is based, in some embodiments, on the volume velocity (V), the percentage of partial occlusion of the IJV, length of time (T) and in appropriate embodiments the given DV pressure applied.

One particular useful output for physicians and other health care professionals or assistants from the system 10 of the present invention is the absolute length of time (T), for example in seconds or milliseconds, from the partial occlusion of the IJV until the compression of the waveform variability characteristic (i.e. amplitude, an area under the curve, dominant frequency, direction of high frequency shift, a phase shift or a multiaxial spectroscopy of the waveform). Another useful output for physicians and other health care professionals or assistants from the system 10 of the present invention is the relative length of time (T), for example in seconds or milliseconds, from the partial occlusion of the IJV until the compression of the waveform variability characteristic (i.e. amplitude, an area under the curve, dominant frequency, direction of high frequency shift, a phase shift or a multiaxial spectroscopy of the waveform) compared to a previous measurement, for example a recent measurement using the present invention. Another useful output for physicians and other health care professionals or assistants from the system 10 of the present invention is a determination whether the length of time (T) from the partial occlusion of the IJV until the compression of the waveform is within a particular range of time, or in other embodiments is equal to a specific scalar time quantity, for example a time in seconds or milliseconds that is considered normal for a person's ICRS to become "occupied" upon commencement of partial occlusion of the IJV. This "normal" time may depend on the age of the individual. This "normal" time may depend on other characteristics of the individual, such as normality of ICP level and age. For example, many, although not all, elderly people experience atrophy of the brain tissue and this generates a larger space or ICRS. Similarly, elevated ICP is associated with smaller ICRS. Accordingly, one is able to create handy physical charts or digital charts or look-up tables or other data that in some cases is provided to computer system 50 that provide the "normal" length of time expected for "occupying" the ICRS upon partial occlusion of IJV based on one or more other parameters such as age, health including the existence of an intracranial growth, a pathology, ICP or another parameter. The "normal" times can be simple magnitudes or can be ranges of magnitudes, for example 3 to 5 seconds.

In some embodiments, the specific scalar normal time quantity is 2 seconds or 3 second or 2.5 seconds or anything between 2 and 3 seconds or another scalar time amount greater than 3 seconds or less than 2 seconds. The time represents the "normal" expected amount of time for the ICRS to become occupied by the blood flow blocked at the IJV for a healthy person, possibly at a given age. This time would in some embodiments also take into consideration the pressure applied to the IJV, for example the pressure applied at the time the predefined amount of compression of the ICP waveform occurs. When compression is referred to, what is meant here is decline in variability of a waveform parameter to a predefined degree.

As mentioned, the variability of the waveform characteristic, for example amplitude, is defined for example as a difference between the highest and lowest amplitude (or other characteristic) during a set cycle of say 10 milliseconds from the partial occlusion—called the initial variability or the variability at the first cycle. Then the variability of the ICP waveform during each subsequent time cycle, for example each subsequent 10 milliseconds, is monitored from when the partial occlusion of the IJV commenced. Then, when the variability of the waveform has reached a predefined percentage lower than the original variability, the predefined amount of compression of the waveform has been deemed to have occurred and that represents the end time (the start time being the commencement of the partial occlusion) for purposes of measuring the length of time (T), one of the ICRS parameters used in the present invention.

The IJV is therefore monitored to see when the partial occlusion begins since the partial occlusion does not commence the instant that pressure is applied to the skin above the IJV by the instrument 30 of system 10, although it typically takes less than a second for partial occlusion to occur from when such pressure is applied to the skin. This partial occlusion is visually detectable by a user on an image of the IJV derived from the ultrasound probe converted to a display, or automatically by the software 55 of computer system 50 such as special purpose software. In order to achieve the desired degree of partial occlusion, for example between 5% and 15%, or in other non-limiting examples between 5% and 10%, a small amount of time elapses after commencement of pressure on the skin above the IJV. The time of commencement of actual partial occlusion of the IJV is determined by the computer system that receives ultrasound images of the IJV.

Another particularly useful output provided in some embodiments by the computer system 50 is the ICRS capacity as determined from the blood flow blocked at the IJV. One can create handy charts or digital charts or look-up tables correlating the "normal" ICRS capacity as determined by partial occlusion of the IJV based on age and other parameters, such as health, pathology, ICP or otherwise, to which the actual measurements can be compared.

From the output of the intracranial reserve space parameter, which may be the length of time (T) or the ICRS capacity or the ICRS/ICP, the one or more processors of the computer system are configured in some cases to determine a suspicion that clinical deterioration of the subject either occurred or is predicted to occur.

Applicant believes that it is preferable using the systems and methods of the present invention to partially occlude the internal jugular vein on the right side of the neck rather than on the left side, although the present invention may certainly be implemented by partial occlusion of the internal jugular vein on the right side or the left side, and in some embodiments partial occlusion is performed on one side and later on the opposite side. Recent published articles of Igor D. Stulin (Zh Nevrol Psikhiatr Iiri S S Korsakova 2014; 114(5):39-41) observe a physiological asymmetry of the IJV. Applicant believes based on these articles that the ICRS parameters obtained by the present invention would be more precise if the partial occlusion is on the right side since the right IJV is straighter than the left IJV and thereby enters the heart more directly. Secondly, Applicant also believes that partial occlusion of the right IJV is safer because of its wider diameter according to the asymmetry found by Stulin and others, at least for most patients. However, if it is learned by ultrasound or otherwise that for a given patient the asymmetry is such that the left jugular vein is wider in diameter, then in some embodiments the left IJV is used, although in other embodiments the right IJV is used.

When partial occlusion is continued beyond the subsequent time (T) at which the waveform is sufficiently compressed so as to exhibit a predefined decline in variability, a normal healthy person would be expected to experience a cerebral venous blood flow autoregulation mechanism whereby the internal jugular vein located on the opposite side of the neck from the IJV that was partially occluded, expands in diameter and brain tissue pulsation returns to normal. What happens is that the venous blood blocked in one hemisphere of the brain from exiting moves to the other hemisphere of the brain through the superior sagittal sinus vein (SSS) and exits through venous shunts that have sprouted into bridging veins between the intracranial and extra-cranial areas.

Figure 10:
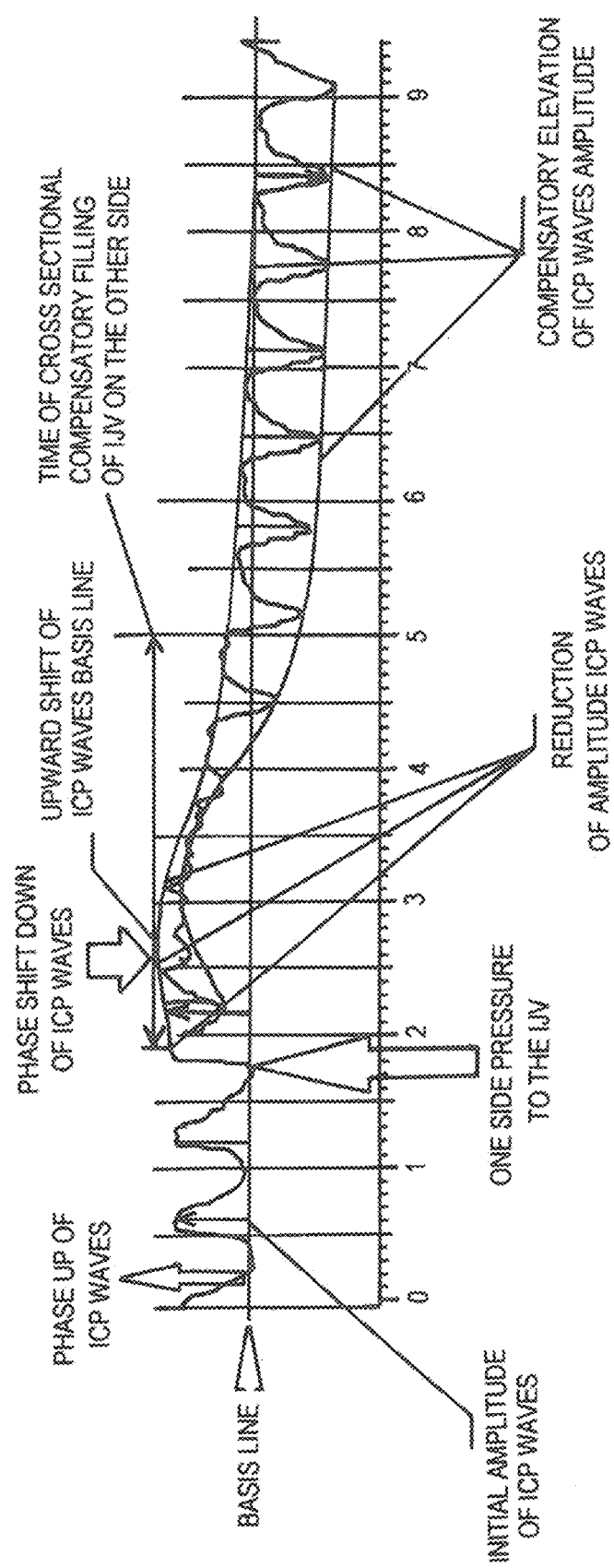
FIG. 10 is a graph of ICP amplitude of a patient from a time of pressure applied to the internal jugular vein (IJV) showing compression of variability of ICP waveform and until natural recovery of amplitude variability (vascular cross filling time—VCFT) by means of the ITV on the opposite side of the neck of the patient, in accordance with one embodiment of the present invention.

FIG. 10 depicts the amplitude of the ICP waveform from when t=0. At about t=1.6 seconds, partial occlusion of the internal jugular vein on one side of the neck is performed. There is an upward shift in basis line after that. At approximately t=3.25 seconds, the predefined decline in variability of the ICP wave amplitude has occurred. From approximately t=3.25 seconds until a normalization time at approximately t=6.5 seconds, the partial occlusion is continued and as shown in FIG. 10, the cross-filling time during which normalization of the ICP wave amplitude variability is restored occurs. The part of the venous flow autoregulation time (also called cross-filling time) that is after the predefined decline in variability of the ICP waveform is referred to herein as the "further length of time" to distinguish it from the "length of time (T)" that encompasses the interval running from the partial occlusion of the IJV until the predefined decline in variability of the ICP waveform. In this case, FIG. 10 shows that this "further length of time" for normalization after the predefined decline in variability took about 3.25 seconds.

Accordingly, in some embodiments, the computer system is configured to determine a "further length of time" beginning from the time at which the waveform is sufficiently compressed so as to exhibit the predefined decline in variability to a normalization time at which the predefined decline in variability has been reversed (brain tissue pulsation has been restored), the reversal such that a variability of the waveform at the normalization time equals, within a predefined degree of accuracy, a variability of the waveform at the start time. The normalization time has occurred when either (i) the amplitude of the ICP waveform returns to equal what it was at the start of the partial occlusion (i.e. equal to within a predefined level of accuracy) or (ii) the variability of the ICP waveform returns to be equal to what it was at the start of the partial occlusion, within a predefined level of accuracy. Note that the variability of the ICP waveform is measured using any of the same parameters used to measure the variability of the ICP waveform when determining the predefined decline in variability. The "further length of time" is defined as the time interval from the "subsequent time (T) at which the waveform is sufficiently compressed so as to exhibit a predefined decline in variability" until the "normalization time". The term "subsequent time" was used simply because it was subsequent to the start time of the partial occlusion and was used as the endpoint of the length of time used to measure the ICRS parameter. In some embodiments, the predefined level of accuracy is to within 5% and in other embodiments the predefined level of accuracy is to within 1% or 3% or 7% or 10% or 15% or 20% or 30% or 50% or a different percentage between 1% and 50%.

Accordingly, in some embodiments, the computer system 50 is configured to send an alert predicting future clinical deterioration of the subject if the further length of time is excessive or too short relative an expected normal further length of time. The expected "further length of time" for healthy individuals may vary depending on a number of factors but on average for adults it is approximately two to four seconds and about three seconds. In addition, the expected normal "further length of time" for normalization is in some embodiments determined based on what is expected normal for that particular patient from prior investigation of that patient rather than by comparing the particular patient to the population based on age or other factors.

Accordingly, in cases in which the ICRS parameter is found to be normal when checking a specific patient with the present invention, if the "further length of time" to reach normalization, i.e. to restore brain tissue pulsation, is excessive or short, the system 10 of the present invention is configured in certain embodiments to send an alert. This alert in some embodiments predicts clinical deterioration of the patient. Since occupation of the ICRS has not yet occurred, the predicted future clinical deterioration is not immediate clinical deterioration but rather is more distant than "immediate, for example a day or two in the future. Thus, this further length of time is an even earlier predictor or marker for future clinical deterioration of a patient than the length of time until the ICRS is occupied.

In some embodiments, system 10 or it components (probe 20, instrument 30 including second probe 35A, computer system 50) is utilized in accordance with any of the steps or actions described below in relation to method 100.

In one embodiment, the present invention is a system for non-invasive monitoring of an intracranial reserve space (ICRS) parameter of a mammalian subject, comprising: a multi-frequency ultrasound probe configured, beginning at a start time, to emit and receive ultrasound waves into and from a head of the subject and to produce a signal of brain tissue pulsation; an instrument configured to non-invasively apply a pressure to effectuate a partial occlusion of the cross-section of an internal jugular vein of the subject, the partial occlusion starting at the start time, the instrument including a second ultrasound probe configured to produce a second signal for imaging a cross-section of the internal jugular vein, the second ultrasound probe having a Doppler ultrasound output for measuring a linear velocity of venous blood at the internal jugular vein; and a computer system configured to receive the signal and an output of the start time of the partial occlusion of the internal jugular vein of the subject. The computer system 50 is also configured to receive the second signal and to derive from the second signal an image of the internal jugular vein, for example the cross-section of the IJV and to determine the linear velocity of venous blood at the IJV.

The computer system is also configured, using one or more processors, to derive from the signal an intracranial brain tissue pulsation waveform, and to determine an ICRS capacity from (i) a length of time (T) from the start time to a subsequent time at which the waveform is sufficiently compressed so as to exhibit a predefined decline in variability and from (ii) a volume velocity (V) of blocked venous blood output occluded at the IJV, wherein the volume velocity is determined by the computer system from the linear velocity of the internal jugular vein derived from the Doppler ultrasound output and from the image(s) of the cross-section of the internal jugular vein.

The present invention, in one embodiment, is a method 100 of non-invasively monitoring an intra-cranial reserve space parameter of a mammalian subject. Method 100 comprises a step 110 of using a probe to emit and receive ultrasound frequency waves into and from a body part, for example a head, of the subject during a time interval and to produce a signal corresponding to pulsation of brain tissue of the subject. The probe, in one embodiment, is a two-dimensional probe with a lower emitter frequency than the receiver frequency. For example, the emitter may emit at 0.5-3 MHZ while the receiver receives at approximately 1.0 MHz-6 MHz, which provides a high resolution scan. In some embodiments, the probe 20 has any of the characteristics mentioned in regard to probe 20 of system 10.

Method 100 comprises a step 120, in one embodiment, of applying an instrument 30 such as instrument 30 of system 10 to a neck of the subject to non-invasively partially occlude an internal jugular vein of the subject, the partial occlusion starting at a start time of the time interval. In some embodiments of method 100 the instrument 30 has any of the characteristics described in relation to instrument 30 of system 10. An example of the instrument 30 is a device such as shown in FIG. 6 and FIG. 8 comprising for example a step-wise motor, syringe for housing at least one piston and a fluid pump for a fluid such as air. The instrument 30 applies the pressure by applying an initial pressure and then increasing the pressure from the initial pressure stepwise in uniform increments until the predefined decline in variability occurs. The instrument 30, in one particular embodiment, also has attached to it, for example at the other end away from the subject, a manometer for measuring the pressure.

The measured internal jugular venous pressure (IJVP) by manometer 39 of instrument 30 is substantially equal to the subject's ICP at a moment that the amplitude (or other ICP wave variability parameter) of the ICP waves starts to decline. The reason for this is that at that point the pressure of the blood in the cranium is substantially equal to the pressure against the blood in the cranium.

Accordingly, in one embodiment step 120 comprises: using an instrument, non-invasively applying a pressure to a neck of the subject to effectuate a partial occlusion of an internal jugular vein of the subject, the partial occlusion starting at a start time of the time interval, the instrument measuring the pressure and including a distal ultrasound probe configured for producing a second signal for imaging the internal jugular vein, for example for imaging a cross-section of the internal jugular vein or another view of the internal jugular vein that allows monitoring of the cross-section or diameter of the internal jugular vein (or allows monitoring some other parameter of the IJV sufficient to reveal when the partial occlusion has started).

Method 100 has a step 130, in one embodiment, of receiving, by means of a computer system, the signal from the ultrasound probe 20 (i.e. the probe applied to the subject's head) and deriving from this signal an intracranial brain tissue pulsation waveform of the tissue pulsation of the subject, for example in the cranium of the subject. In certain embodiments, the computer system is also configured to receive an output of the start time of the interval from when partial occlusion of the internal jugular vein commenced.

In some embodiments, step 130 also comprises the computer system receiving the second signal and deriving from the second signal images of the internal jugular vein, for example its cross-section, and in some cases determining the extent of the partial occlusion (for example the partial cross-sectional occlusion) of the IJV.

In certain embodiments of method 100, there is a further step 140 of determining, by means of one or more processors of the computer system, a length of time (T) from the start time of the interval (when the partial occlusion commenced) to a time when the ICP waveform substantially straightens, that is when the waveform is sufficiently compressed so as to exhibit a predefined decline in variability. The variability of the waveform comprises at least one of the following parameters: (i) a variability of an amplitude of the waveform and (ii) a variability of an area under the curve of the waveform, (iii) a variability of a dominant frequency of the waveform, (iv) a direction of high frequency shift of the waveform, (v) a phase shift of the waveform and (vi) a variability of a multiaxial spectroscopy of the waveform. In another embodiment, variability of the intracranial brain tissue pulsation waveform comprises a variability of at least one of the following ICP waveform parameters: (i) an amplitude of the waveform and (ii) an area under the curve of the waveform, (iii) a dominant frequency of the waveform (for example a frequency between 0.1 and 35 MHz) and (iv) and (vi) a multiaxial spectroscopy of the waveform (ICPWMS). The spectroscopy referred to herein is a mechanical motion (pulsatility) spectroscopy, not a magnetic or electrical spectroscopy. Other functions that indicate variability of the ICP waveform are also within the method of the present invention, including but not necessarily limited to combinations and/or derivatives of the above six examples of ICP waveform variability indicia/parameters.

Steps 110, 120, 130 and 140 of method 100 in some embodiments are repeated dynamically at least once (for example after an interval of minutes or hours or a day or days). The results of the two or more measurements of the ICRS parameter are compared to determine if there has been a change in length of time (T) or a change in the ICRS capacity.

In some embodiments, there is a step of determining by means of one or more processors of the computer system 50, the ICRS capacity based on the volume velocity (V) multiplied by time (T) and multiplied by the percentage of the ITV that has been partial occluded. In still other embodiments, there is step of determining the ICRS (i.e. the ICRS capacity) divided by the intracranial pressure.

In some embodiments, there is step of converting the signal from the ultrasound probe applied of the head of the subject into a dynamic image of a pulsatility of brain tissue, wherein the image is of the sector of the head that the multi-frequency ultrasound probe received ultrasound waves from.

In some embodiments, there is a step of providing an output, to the physician or other user, of the ICRS parameter, for example the ICRS capacity, the length of time (T), and/or the ICRS capacity divided by intracranial pressure of the subject or another useful parameter and to provide such output dynamically and/or repeatedly, such as every minute or every 5 or 10 or 20 or 30 or 40 or 50 minutes or every hours or every several hours or every 3 or 4 or 5 or 6 or 9 or 12 hours or every day or every 2 or 3 or 3 or 4 or 5 or 7 or 10 days or every two weeks or every month. The computer system in some embodiments also determines that the subject has an abnormal intracranial reserve space and/or that clinical deterioration is either predicted to occur or inferred to have occurred.

Method 100 results in a length of time ($T_1$) having been determined. In some embodiments, method 100 is repeated and a further or subsequent length of time ($T_2$) is determined. In some embodiments, the method 100 is repeated and predicts at least one of (i) elevated ICP and (ii) clinical deterioration of the patient, if the subsequent length of time ($T_2$) is less than the length of time ($T_1$) by a predefined amount (the term "amount" including both absolute amounts and relative amounts). The predefined amount can be a percentage or an absolute amount suitably determined based on age, medical condition and any other suitable factor. For example the predefined amount in some embodiments is a one-third decline or a 40% decline in the length of time, or 50%, or 60%, or 70%, or 80%, or 90%, or 100%, or a greater or lower percentage decline or some other numerical percentage between one-third and 100%, or a decline of at least a predefined absolute amount such as at least one half a second, at least three-quarters of a second, at least one second, at least 1.5 seconds at least 2 seconds, at least 2.5 seconds, at least 3 seconds or at least 3.5 or at least 4 seconds or any number in between 1 second and 4 second or greater than 4 seconds.

The method 100, or a variation thereof in which the ICRS parameter is the ICRS capacity rather than the length of time (T), may be performed and then repeated within a relative short interval dynamically with the results compared to determine if there has been a sudden or recent occupying of the ICRS.

The method 100 of the present invention in some embodiments has any of the characteristics described in relation to system 10. For example, in some embodiments of method 100, the multi-frequency ultrasound probe 20 is configured to receive ultrasound waves from at least two different intracranial locations, as discussed in relation to system 10. In another example, in some embodiments, method 100 comprises sending an alert predicting at least one of (i) an elevated intracranial pressure and (ii) clinical deterioration of the subject, wherein the computer system may be configured to send the alert based on the length of time (T), the ICRS capacity and/or a given intracranial pressure applied.

The following is an example of an experimental use of one aspect of the claimed invention. An elderly human subject is admitted for treatment to a hospital, reporting a fall. The intracranial reserve space of the subject was measured. The computer system 50 outputs that it took 8 seconds for the ICRS of the subject to be occupied, which indicates high grade brain atrophy. A CT was run and it revealed mild subarachnoid and mild intraparenchymal hemorrhage right parietal. This does not justify surgery. During observation, the intracranial reserve space was re-measured about three hours after the first CT. The ICRS takes only 4 seconds to become occupied according to the second measurement. This indicates a growth of the volume of the hemorrhage, or brain swelling. A second CT was run even though only three hours had elapsed from the first CT, which is not the norm at least according to the guidelines of the American Academy of Neurology, since 6 hours had not elapsed. The information from the second ICRS measurement indicated the need for the second CT. The second CT revealed a large hemorrhage. Surgery was performed, including a right parietal craniotomy and removal of the intracranial hemorrhage.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A system for non-invasive monitoring of an intracranial reserve space (ICRS) parameter of a mammalian subject, comprising:

an at least two-dimensional multi-frequency ultrasound probe configured, beginning at a start time, to emit and receive ultrasound waves into and from a head of the subject and to produce a signal of intracranial brain tissue pulsations in at least a horizontal spatial and a vertical spatial dimension, the brain tissue pulsations responsive to pulses of a heart systole and/or arterial pressure;

an instrument configured to non-invasively apply a pressure to a neck of the subject effectuate a partial occlusion of an internal jugular vein of the subject, the partial occlusion staffing at the start time, the instrument including a second ultrasound probe configured to produce a second signal for imaging the internal jugular vein the instrument including a pressure applying component having at least one surface configured to contact the neck and including a manometer; and a computer system configured to receive the signal and an output, of the start time of the partial occlusion of the internal jugular vein of the subject, the computer system also configured, using one or more processors, to derive from the signal of intracranial brain tissue pulsations an intracranial brain tissue pulsation waveform, and to determine a length of time front the start time to a subsequent time at which the waveform is compressed so as to exhibit a predefined decline in variability, the predefined decline in variability being an amount that is 5% or more, the computer system also configured to receive the second signal and to derive from the second signal images of the internal jugular vein.

2. The system of claim 1, wherein the multi-frequency ultrasound probe emits in transmission mode at an emitter frequency and the probe receives at a receiver frequency such that the emitter frequency is lower than the receiver frequency.

3. The system of claim 1, wherein the instrument is configured to apply an initial pressure and subsequent greater pressures in uniform increments to the internal jugular vein.

4. The system of claim 1, wherein the instrument includes a motor or a compressor, at least one piston movable within a housing, and an applicator that includes the second ultrasound probe, a distal end of the applicator shaped to engage the neck of the subject.

5. The system of claim 1, wherein the multi-frequency ultrasound probe has a piezoelectric array configured to adapt to a shape of the skull.

6. The system of claim 1, wherein the multi-frequency ultrasound probe emits at a frequency of 0.5 to 3 MHz and receives at a frequency of 1.0 MHz to 6.0 MHz.

7. The system of claim 1, wherein an end of the multi-frequency ultrasound probe is shaped to conform to a skull and wherein the ultrasound probe emits at a frequency of about 1.0 MHz and receives at a frequency of up to 1.76 MHz using a carrier frequency of about 0.5 MHz to 1.76 MHz.

8. The system of claim 1, wherein variability of the waveform comprises at least one of the following parameters: (i) a variability of an amplitude of the waveform (ii) a variability of an area under the curve of the waveform, (iii) a variability of a dominant frequency of the waveform (iv) a direction of high frequency shift of the waveform, (v) a phase shift of the waveform and (vi) a variability of a multiaxial spectroscopy of the waveform.

9. The system of claim 1, wherein the computer system is further configured to convert the signal into a dynamic image of a multiaxial pulsatility of brain tissue in at least a part of the head that the probe received ultrasound waves from.

10. The system of claim 1, wherein the computer system is configured to predict an elevated ICP of the subject, the prediction being derived from the determination of an intracranial reserve space (ICRS) parameter, wherein the ICRS parameter is at least one of (i) the length of time (T) and (ii) the intracranial reserve space (ICRS) capacity.

11. The system of claim 1, wherein the computer system is further configured to determine a magnitude of an intracranial reserve space (ICRS) parameter during the length of time (T).

12. The system of claim 1, wherein the computer system is configured to determine a magnitude of an ICRS capacity based on a volume velocity (V) of blocked venous blood output occluded at the IJV multiplied by the length of time (T).

13. The system of claim 1, wherein the computer system is configured to send an alert based on at least one of: the length of time (T) and an intracranial reserve space capacity.

14. The system of claim 1, wherein the multi-frequency ultrasound probe is configured to receive ultrasound waves from at least two different intracranial locations.

15. The system of claim 14, wherein the computer system is configured to determine a representative ICRS parameter from separate respective ICRS magnitudes at the at least two different intracranial locations.

16. The system of claim 1, wherein one or more processors of the computer system are configured to determine an ICRS parameter from a relationship of $\Delta V/\Delta P$.

17. The system of claim 1, wherein one or more processors of the computer system is configured to determine that an elevated intracranial pressure either occurred or is predicted.

18. The system of claim 1, wherein the multi-frequency ultrasound probe is configured to operate in both a transmission mode and an impulse mode such that one of the (i) emitter and (ii) receiver operates in transmission mode and another of the (i) emitter and (ii) receiver operates in impulse mode.

19. The system of claim 1, wherein the computer system is configured to determine a further length of time beginning from the time at which the waveform is compressed so as to exhibit the predefined decline in variability to a normalization time at which the predefined decline in variability has been reversed, the reversal such that a variability of the waveform at the normalization time equals, within a predefined degree of accuracy, a variability of the waveform at the start time.

20. A system for non-invasive monitoring of an intracranial reserve space (ICRS) parameter of a mammalian subject, comprising:
a multi-frequency ultrasound probe configured, beginning at a start time, to emit and receive ultrasound waves into and from a head of the subject and to produce a signal of brain tissue pulsation;
an instrument configured to non-invasively apply a pressure to a neck of the subject to effectuate a partial occlusion of a cross-section of an internal jugular vein of the subject, the partial occlusion starting at the start time, the instrument including a second ultrasound probe configured to produce a second signal for imaging a cross-section of the internal jugular vein, the second ultrasound probe having a Doppler ultrasound output for measuring a linear velocity of venous blood at the internal jugular vein, the instrument including a pressure applying component having at least one surface configured to contact the neck and including a manometer; and
a computer system configured to receive the signal and an output of the start time of the partial occlusion of the internal jugular vein of the subject, the computer system also configured to receive the second signal and to derive from the second signal an image of the cross-section of the internal jugular vein and to determine the linear velocity of venous blood at the internal jugular vein, the computer system also configured, using one or more processors, to derive from the signal an intracranial brain tissue pulsation waveform, and to determine an ICRS capacity from (i) a length of time (T) from the start time to a subsequent time at which the waveform is compressed so as to exhibit a predefined decline in variability, the predefined variability being an amount that is 5% or more, and from (ii) a volume velocity (V) of blocked venous blood output occluded at the IJV, wherein the volume velocity is determined by the computer system from the linear velocity of the internal jugular vein derived from the Doppler ultrasound output and from the image of the cross-section of the internal jugular vein.

* * * * *